(12) United States Patent
Hoshino et al.

(10) Patent No.: US 10,233,331 B2
(45) Date of Patent: Mar. 19, 2019

(54) FLUORINATED ETHER COMPOSITION, METHOD FOR ITS PRODUCTION, COATING LIQUID, SUBSTRATE HAVING SURFACE-TREATED LAYER AND METHOD FOR ITS PRODUCTION

(71) Applicant: Asahi Glass Company, Limited, Chiyoda-ku (JP)

(72) Inventors: Taiki Hoshino, Chiyoda-ku (JP); Eisuke Murotani, Chiyoda-ku (JP); Akira Isobe, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 171 days.

(21) Appl. No.: 15/163,198

(22) Filed: May 24, 2016

(65) Prior Publication Data
US 2016/0264788 A1 Sep. 15, 2016

Related U.S. Application Data

(63) Continuation of application No. PCT/JP2014/082648, filed on Dec. 10, 2014.

(30) Foreign Application Priority Data

Dec. 13, 2013 (JP) ................................ 2013-258414
Dec. 13, 2013 (JP) ................................ 2013-258415

(51) Int. Cl.

| | |
|---|---|
| C09D 4/00 | (2006.01) |
| C07F 7/08 | (2006.01) |
| C23C 16/56 | (2006.01) |
| C04B 41/82 | (2006.01) |
| C08G 65/00 | (2006.01) |
| C08L 71/02 | (2006.01) |
| C08G 65/336 | (2006.01) |
| C09D 171/02 | (2006.01) |
| C09D 7/40 | (2018.01) |
| C09D 5/00 | (2006.01) |

(52) U.S. Cl.
CPC .............. *C09D 4/00* (2013.01); *C04B 41/82* (2013.01); *C07F 7/081* (2013.01); *C07F 7/0829* (2013.01); *C08G 65/007* (2013.01); *C08G 65/336* (2013.01); *C08L 71/02* (2013.01); *C09D 5/00* (2013.01); *C09D 7/40* (2018.01); *C09D 171/02* (2013.01); *C23C 16/56* (2013.01)

(58) Field of Classification Search
None
See application file for complete search history.

(56) References Cited

U.S. PATENT DOCUMENTS

| | | | |
|---|---|---|---|
| 3,810,874 A | 5/1974 | Mitsch et al. | |
| 6,248,915 B1 * | 6/2001 | Ito ........................ | C08G 65/336 |
| | | | 528/15 |
| 9,388,315 B2 * | 7/2016 | Hoshino ................... | C09D 4/00 |
| 2003/0226818 A1 * | 12/2003 | Dunbar .................. | B81B 3/0005 |
| | | | 216/20 |
| 2013/0228100 A1 | 9/2013 | Kleyer et al. | |
| 2014/0202355 A1 | 7/2014 | Hoshino | |
| 2015/0307719 A1 * | 10/2015 | Mitsuhashi .............. | C09D 5/16 |
| | | | 428/447 |

FOREIGN PATENT DOCUMENTS

| | | |
|---|---|---|
| JP | 10-72568 | 3/1998 |
| WO | WO 2009/008380 A1 | 1/2009 |
| WO | WO 2011/059430 A1 | 5/2011 |
| WO | WO 2012/064989 A1 | 5/2012 |
| WO | WO 2013/042732 A1 | 3/2013 |
| WO | WO 2013/042733 A1 | 3/2013 |
| WO | WO 2013/121986 A1 | 8/2013 |

OTHER PUBLICATIONS

International Search Report dated Mar. 17, 2015 in PCT/JP2014/082648 filed on Dec. 10, 2014.
U. Mayer, "Ionic Equilibria in Donor Solvents", Pure & Appl. Chem., vol. 41, (3), 1975, 36 pgs.
Ingmar Persson, "Solvation and complex formation in strongly solvating solvents", Pure & Appl. Chem., vol. 58, (8), 1986, 9 pgs.
U.S. Appl. No. 14/221,609, filed Mar. 21, 2014, Patent No. 2014/020235 A1, Taiki Hoshino.
U.S. Appl. No. 14/311, 948, filed Jun. 23, 2014, Patent No. 2014/0302332 A1, Eisuke Murotani, et al.
U.S. Appl. No. 14/298,643, filed Jun. 6, 2014, Patent No. 2014/0287246 A1, Eisuke Murotani et al.
U.S. Appl. No. 14/298,267, filed Jun. 6, 2014, Patent No. 2014/0287240 A1, Eisuke Murotani, et al.
U.S. Appl. No. 14/862,613, filed Sep. 23, 2015, Patent No. 2016/0009929 A1, Taiki Hoshino, et al.

* cited by examiner

*Primary Examiner* — Nicole M. Buie-Hatcher
(74) *Attorney, Agent, or Firm* — Oblon, McClelland, Maier & Neustadt, L.L.P.

(57) ABSTRACT

To provide a fluorinated ether composition useful for surface treatment to impart water/oil repellency to the surface of a substrate, a method for producing the fluorinated ether composition, and a coating liquid containing the fluorinated ether composition, as well as a substrate having a surface-treated layer, and a method for producing the same. Said composition comprises at least two fluorinated ether compounds which are represented by $A\text{-}O\text{-}Q\text{-}(C_bF_{2b}O)_d\text{-}X\text{-}O\text{-}B^{10}$ and which are different in $B^{10}$. X is a divalent organic group having no $CF_2O$. $B^{10}$ is $-CH_2CH_2CH_2SiL_mR_n$, $-CH_2CH(SiL_mR_n)CH_3$, $-CH_2CH=CH_2$ or $-CH=CHCH_3$. A is a perfluoroalkyl group or group $B^{10}$. Of the total of group $B^{10}$ in said composition, the proportion of $-CH_2CH_2CH_2SiL_mR_n$ is from 90 to 99 mol %, and the proportion of $-CH=CHCH_3$ is from 1 to 10 mol %. L is a hydrolyzable group, and R is a monovalent hydrocarbon group. b is an integer of from 1 to 10, and d is an integer of from 1 to 200.

24 Claims, No Drawings

FLUORINATED ETHER COMPOSITION, METHOD FOR ITS PRODUCTION, COATING LIQUID, SUBSTRATE HAVING SURFACE-TREATED LAYER AND METHOD FOR ITS PRODUCTION

TECHNICAL FIELD

The present invention relates to a fluorinated ether composition which is useful for surface treatment to impart water/oil repellency on the surface of a substrate, a method for producing the fluorinated ether composition, and a coating liquid containing the fluorinated ether composition. The present invention relates to a method for producing a substrate having a surface-treated layer by using the fluorinated ether composition or the coating liquid, and a substrate having a surface-treated layer produced by such a method.

BACKGROUND ART

Fluorinated compounds show high lubricity, water/oil repellency, etc. and are thus useful for surface treatment agents. When water/oil repellency is imparted to the surface of a substrate by such surface treatment agents, it becomes easier to wipe off dirt on the surface of the substrate, whereby removability of stains will be improved. Among fluorinated compounds, a fluorinated ether compound having a poly(oxy perfluoroalkylene) chain, wherein an ether bond (—O—) is present in the perfluoroalkylene chain, is a compound excellent in flexibility, which is particularly excellent in removability of stains of e.g. fats and oils.

It is known to use a composition containing a fluorinated ether compound which has a poly(oxyperfluoroalkylene) chain and has a hydrolyzable silyl group at its terminal, as a surface treatment agent such as an antifouling agent, a lubricant or a water/oil repellent (see Patent Documents 1 and 2.).

PRIOR ART DOCUMENTS

Patent Documents

Patent Document 1: WO2011/059430
Patent Document 2: WO2013/042733

DISCLOSURE OF INVENTION

Technical Problem

However, according to the findings of the present inventors, the surface-treated layer formed by using the composition containing the fluorinated ether compound as disclosed in each of Patent Documents 1 and 2, was sometimes insufficient in abrasion resistance.

It is an object of the present invention to provide a fluorinated ether composition capable of forming a surface-treated layer which can impart excellent water/oil repellency on the surface of a substrate, and which is excellent in abrasion resistance, whereby the water/oil repellency is less likely to be lowered even by repeated abrasion, a method for producing such a fluorinated ether composition, and a coating liquid containing such a fluorinated ether composition.

It is another object of the present invention to provide a method for producing a substrate having a surface-treated layer which can impart excellent water/oil repellency on the surface of a substrate, and which is excellent in abrasion resistance, whereby the water/oil repellency is less likely to be lowered even by repeated abrasion, and to provide a substrate having a surface-treated layer, produced by such a method.

Solution to Problem

The present invention provides a fluorinated ether composition, a method for its production, a coating liquid, a substrate having a surface-treated layer, a method for its production and a touch panel, having the following constructions [1] to [15].

[1] A fluorinated ether composition comprising at least two fluorinated ether compounds which are represented by the following formula (1) and which are different in group $B^{10}$, wherein, of the total of group $B^{10}$ present in said composition, the proportion of a group represented by the following formula (2-1) is from 90 to 99 mol %, the proportion of a group represented by the following formula (2-2) is from 0 to 9 mol %, the proportion of a group represented by the following formula (2-3) is from 0 to 9 mol %, and the proportion of a group represented by the following formula (2-4) is from 1 to 10 mol %:

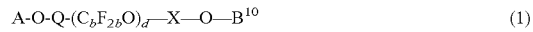
$$\text{A-O-Q-}(C_bF_{2b}O)_d\text{—X—O—}B^{10} \tag{1}$$

the symbols in the formula (1) represent the following:

A: a $C_{1-20}$ perfluoroalkyl group or the following $B^{10}$,

Q: a single bond, —$CH_2$—, —CHF—, -$Q^1$-$CH_2$—, -$Q^1$-CHF—, -$Q^1O$—$CH_2$—, -$Q^1$-O—CHF—, -$Q^1$-$CH_2$—O— or -$Q^1$-CHF—O—, $Q^1$: a $C_{1-10}$ fluoroalkylene group, a $C_{2-10}$ fluoroalkylene group having an etheric oxygen atom between carbon-carbon atoms, a $C_{1-10}$ alkylene group, or a $C_{2-10}$ alkylene group having an etheric oxygen atom between carbon-carbon atoms, b, d: b is an integer of from 1 to 10, and d is an integer of from 1 to 200, provided that when d is at least 2, $(C_bF_{2b}O)_d$ may be composed of at least two types of $C_bF_{2b}O$ different in b, X: a divalent organic group having no $CF_2O$, $B^{10}$: a group represented by the following formula (2-1), a group represented by the following formula (2-2), a group represented by the following formula (2-3) or a group represented by the following formula (2-4):

$$\text{—}CH_2CH_2CH_2SiL_mR_n \tag{2-1}$$

$$\text{—}CH_2CH(SiL_mR_n)CH_3 \tag{2-2}$$

$$\text{—}CH_2CH\text{=}CH_2 \tag{2-3}$$

$$\text{—}CH\text{=}CHCH_3 \tag{2-4}$$

the symbols in the formulae (2-1) to (2-4) represent the following:

L: a hydrolysable group,

R: a monovalent hydrocarbon group.

m and n: m is an integer of from 1 to 3, and n is an integer of from 0 to 2, provided m+n=3.

[2] The fluorinated ether composition according to [1], wherein, of the total of group $B^{10}$ present in said composition, the total proportion of the group represented by the above formula (2-1) and the group represented by the above formula (2-4) is from 95 to 100 mol %.

[3] The fluorinated ether composition according to [2], wherein, of the total of group $B^{10}$ present in said composition, the proportion of the group represented by the above formula (2-1) is from 92 to 99 mol %, the proportion of the group represented by the above formula (2-2) is from 0 to 5 mol %, the proportion of the group represented by the above formula (2-3) is from 0 to 5 mol %, and the proportion of the group represented by the above formula (2-4) is from 1 to 8 mol %.

[4] The fluorinated ether composition according to any one of [1] to [3], wherein A is a $C_{1-20}$ perfluoroalkyl group.

[5] A method for producing a fluorinated ether composition as defined in any one of [1] to [4], which has a step of reacting a compound represented by the following formula (3) and the compound represented by the following formula (4) in the presence of a transition metal catalyst (C) and at least one compound (D) selected from the group consisting of nitrogen-containing compounds and sulfur-containing compounds:

$$A^1\text{-O-Q-}(C_bF_{2b}O)_d\text{—X—O—}B^{20} \quad (3)$$

$$HSiL^1{}_mR_n \quad (4)$$

the symbols in the formulae (3) and (4) represent the following:

$A^1$: the same $C_{1-20}$ perfluoroalkyl group as A in the above formula (1) or the following $B^{20}$, Q: the same group as Q in the above formula (1), b, d: the same numerical values as b and d in the above formula (1), respectively, X: the same group as X in the above formula (1), $B^{20}$: a group represented by the above formula (2-3), $L^1$: a hydrolyzable group, R: the same group as R in the above formula (1), m and n: the same numerical values as m and n in the above formula (1).

[6] The method for producing a fluorinated ether composition according to [5], wherein the compound (D) is an aromatic amine compound or a sulfoxide compound.

[7] The method for producing a fluorinated ether composition according to [6], wherein the compound (D) is dimethyl sulfoxide or tetramethylene sulfoxide.

[8] The method for producing a fluorinated ether composition according to any one of [5] to [7], wherein the transition metal catalyst (C) is a platinum catalyst.

[9] The method for producing a fluorinated ether composition according to [8], wherein the transition metal catalyst (C) is a Pt/divinyltetramethyldisiloxane complex or a Pt/tetramethyltetravinylcyclotetrasiloxane complex.

[10] A coating liquid comprising the fluorinated ether composition as defined in any one of [1] to [4], and at least one fluorinated organic solvent (E) selected from the group consisting of a fluorinated alkane, a fluorinated aromatic compound and a fluoroalkyl ether.

[11] A method for producing a substrate having a surface-treated layer, which comprises vacuum vapor depositing the fluorinated ether composition as defined in any one of [1] to [4] on a surface of a substrate.

[12] A method for producing a substrate having a surface-treated layer, which comprises applying the coating liquid as defined in [10] to a surface of a substrate, followed by drying.

[13] The method for producing a substrate having a surface-treated layer according to [11] or [12], wherein the material for the surface of the substrate is metal, plastic, glass, ceramic or a composite material thereof.

[14] A substrate having a surface-treated layer, treated with the fluorinated ether composition as defined in any one of [1] to [4].

[15] A touch panel having, at its input side, a substrate having a surface-treated layer, treated with the fluorinated ether composition as defined in any one of [1] to [4].

Advantageous Effects of Invention

According to the fluorinated ether composition and the coating liquid containing the fluorinated ether composition of the present invention, it is possible to form a surface-treated layer which is able to impart excellent water/oil repellency to the surface of a substrate and which is excellent in abrasion resistance, whereby the water/oil repellency is less likely to be lowered even by repeated abrasion.

According to the method for producing a fluorinated ether composition of the present invention, it is possible to produce a fluorinated coating composition capable of forming a surface-treated layer which is able to impart excellent water/oil repellency on the surface of a substrate and which is excellent in abrasion resistance, whereby the water/oil repellency is less likely to be lowered even by repeated abrasion.

The substrate having a surface-treated layer of the present invention, has a surface-treated layer which is able to impart excellent water/oil repellency on the surface of a substrate and which is excellent in abrasion resistance, whereby the water/oil repellency is less likely to be lowered even by repeated abrasion.

According to the method for producing a substrate having a surface-treated layer of the present invention, it is possible to produce a substrate having a surface treated-layer which is able to impart excellent water/oil repellency on the surface of a substrate and which is excellent in abrasion resistance, whereby the water/oil repellency is less likely to be lowered even by repeated abrasion.

DESCRIPTION OF EMBODIMENTS

In this specification, a compound represented by the formula (1) will be referred to as compound (1). Compounds represented by other formulae will be referred to in the same manner. Further, a group represented by the formula (2-1) will be referred to as group (2-1). Groups represented by other formulae will be referred to in the same manner.

The following definitions of terms apply throughout this specification including claims.

A "hydrolyzable silyl group" means a group capable of forming a silanol group (Si—OH) by hydrolysis. For example, it is —$SiL_mR_n$ in the formula (1).

An "etheric oxygen atom" means an oxygen atom to form an ether bond (—O—) between carbon-carbon atoms.

A "fluoroalkylene group" means a group having some or all of hydrogen atoms in an alkylene group substituted by fluorine atoms, and a "perfluoroalkylene group" means a group having all of hydrogen atoms in an alkylene group substituted by fluorine atoms.

A "fluoroalkyl group" means a group having some or all of hydrogen atoms in an alkyl group substituted by fluorine atoms, and a "perfluoroalkyl group" means a group having all of hydrogen atoms in an alkyl group substituted by fluorine atoms.

In a chemical formula of an oxyperfluoroalkylene group, the oxygen atom shall be placed on the right hand side of the perfluoroalkylene group.

An "organic group" is a group having carbon atom(s).

The "surface-treated layer" means a layer which is formed on the surface of a substrate, from the fluorinated ether composition of the present invention.

[Fluorinated Ether Composition]

The fluorinated ether composition of the present invention (hereinafter referred to also as "the present composition") is a composition comprising at least two fluorinated ether compounds. Said at least two fluorinated ether compounds are respectively represented by the following formula (1) and are different in $B^{10}$ from one another.

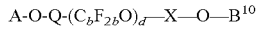

$$A\text{-O-Q-}(C_bF_{2b}O)_d\text{—X—O—}B^{10} \quad (1)$$

The symbols in the formula (1) represent the following:

A: a $C_{1-20}$ perfluoroalkyl group or the following $B^{10}$,

Q: a single bond, —$CH_2$—, —CHF—, -$Q^1$-$CH_2$—, -$Q^1$-CHF—, -$Q^1$-O—$CH_2$—, -$Q^1$-O—CHF—, -$Q^1$-$CH_2$-O— or -$Q^1$-CHF-O—, $Q^1$: a $C_{1-10}$ fluoroalkylene group, a $C_{2-10}$ fluoroalkylene group having an etheric oxygen atom between carbon-carbon atoms, a $C_{1-10}$ alkylene group, or a $C_{2-10}$ alkylene group having an etheric oxygen atom between carbon-carbon atoms, b, d: b is an integer of from 1 to 10, and d is an integer of from 1 to 200, provided that when d is at least 2, $(C_bF_{2b}O)_d$ may be composed of at least two types of $C_bF_{2b}O$ different in b, X: a divalent organic group having no $CF_2O$, $B^{10}$: a group represented by the following formula (2-1), a group represented by the following formula (2-2), a group represented by the following formula (2-3) or a group represented by the following formula (2-4), —$CH_2CH_2CH_2SiL_mR_n$ (2-1).

—$CH_2CH(SiL_mR_n)CH_3$ (2-2).

—$CH_2CH=CH_2$ (2-3).

—CH=CHCH$_3$ (2-4).

The symbols in the formulae (2-1) to (2-4) represent the following:

L: a hydrolysable group,

R: a monovalent hydrocarbon group, m and n: m is an integer of from 1 to 3, and n is an integer of from 0 to 2, provided m+n=3.

The present composition may, for example, be obtained by a hydrosilylation reaction of compound (3) described below and compound (4) described below. In a case where each of compound (3) and compound (4) is substantially one type of compound, individual compound (1) to be produced will be a compound having any one of group (2-1), group (2-2) and group (2-4). Therefore, a reaction product obtainable by the reaction of compound (3) and compound (4) is a mixture of at least two types of compound (1) different in $B^{10}$, as a whole including a compound having unreacted group (2-3).

The present composition is not limited to a composition obtainable in a case where each of compound (3) and compound (4) is substantially one type of compound, and may be a composition composed of a group of at least two types of compound (1) different in $B^{10}$, obtainable by using at least one type of compound (3) and at least one type of compound (4).

In the present composition, with respect to at least one of A, Q, $(C_bF_{2b}O)_d$, X, L and R, there may be at least two different types present. Further, the present composition may be a composition obtained by mixing at least two types of compound (1) which are prepared separately respectively.

Further, the present composition may contain, in addition to compound (1), impurities unavoidable for its production (by-products formed in the production process of the present composition, impurities included, the transition metal catalyst (C) and the compound (D)). The present composition does not contain a liquid medium to be contained in the coating liquid described below. However, in a case where the preparation of the present composition is conducted in the presence of a solvent, the solvent may remain in the present composition. The content of impurities in the present composition is preferably at most 20 mass %, particularly preferably at most 10 mass %. The content of a solvent in the present composition is preferably at most 50 mass %, more preferably at most 30 mass %, particularly preferably at most 5 mass %.

From such a viewpoint that the production is simple and the production cost is low, the present composition is preferably a composition comprising at least two types of compound (1) different in $B^{10}$, obtainable from substantially one type of compound (3) and substantially one type of compound (4).

Group $B^{10}$ $B^{10}$ is group (2-1), group (2-2), group (2-3) or group (2-4).

—$CH_2CH_2CH_2SiL_mR_n$ (2-1).

—$CH_2CH(SiL_mR_n)CH_3$ (2-2).

—$CH_2CH=CH_2$ (2-3).

—CH=CHCH$_3$ (2-4).

Among group (2-1), group (2-2), group (2-3) and group (2-4), group (2-1) and group (2-2) have a hydrolyzable silyl group represented by —$SiL_mR_n$. L is a hydrolyzable group, and the hydrolyzable group becomes a hydroxy group bonded to the silicon atom by a hydrolysis reaction. That is, Si-L becomes a silanol group (—Si—OH) by the hydrolysis reaction. The silanol group can react with a hydroxy group or a silanol group on the surface of a substrate to form a chemical bond, and by this reaction, compound (1) is chemically bonded to the substrate surface. Further, two such silanol groups may undergo an intermolecular or intramolecular dehydration condensation reaction to form a siloxane bond.

Group (2-3) is a terminal group of compound (3) used in the preparation of compound (1), which remained unreacted.

Group (2-4) is a group formed as a by-product during the preparation of compound (1). As group (2-4), there are a cis form (group (2-4d)) and a trans form (group (2-40)), and usually, they are present as mixed.

In the present composition, of the total of group $B^{10}$ present in the composition, the proportion of group (2-1) is from 90 to 99 mol %, the proportion of group (2-2) is from 0 to 9 mol %, the proportion of group (2-3) is from 0 to 9 mol %, and the proportion of group (2-4) is from 1 to 10 mol %. The proportion of group (2-1) is preferably from 92 to 99 mol %. The proportion of group (2-4) is preferably from 1 to 8 mol %.

When the proportion of group (2-1) is within the above range, it is possible to form a surface-treated layer which is able to impart excellent water/oil repellency on the surface of a substrate, and which is excellent in abrasion resistance, whereby the water/oil repellency is less likely to be lowered even by repeated abrasion. That is, excellent water/oil repellency is maintained, not only at the initial stage, but even when repeatedly subjected to abrasion. Further, by containing group (2-1) in a proportion within the above range, and further containing group (2-4) within the above range, it is possible to form a surface-treated layer particularly excellent in abrasion resistance, whereby the water/oil repellency is more unlikely to be lowered even by repeated abrasion.

The present composition is preferably such that, of the total of group $B^{10}$ present in the composition, the total proportion of group (2-1) and group (2-4) is from 95 to 100 mol %. When the total proportion is within the above range, it is possible to form a surface-treated layer, which is excellent in abrasion resistance, whereby the water/oil repellency is more unlikely to be lowered even by repeated abrasion. In the present composition, of the total of group $B^{10}$ present in the composition, the proportion of group (2-2) is preferably from 0 to 5 mol %, more preferably from 0 to 3 mol %, particularly preferably 0 mol %. The proportion of group (2-3) is preferably from 0 to 5 mol %, particularly preferably 0 mol %.

The reason as to why the composition wherein the proportions of groups (2-1) to (2-4) are within the above ranges, is able to form a surface treated layer particularly excellent in abrasion resistance, is considered to be as follows.

Group (2-1) is a group having a hydrolyzable silyl group bonded to a primary carbon atom, whereby it is presumed that compound (1) having such group (2-1) can easily be densely arranged on the surface of a substrate. Therefore, the composition wherein the proportion of group (2-1) is within the above range, is considered to be able to form a surface-treated layer excellent in adhesion to the surface of a substrate and in resistance to abrasion due to repeated abrasion.

Group (2-2) is a group having a hydrolyzable silyl group bonded to a secondary carbon atom, whereby it is presumed that compound (1) having such group (2-2) is less likely to be densely arranged on the surface of a substrate. Therefore, the composition wherein the proportion of group (2-2) is within the above range, is considered to be able to form a surface-treated layer excellent in adhesion to the surface of a substrate and in resistance to abrasion due to repeated abrasion.

Group (2-3) does not have a hydrolyzable silyl group and is therefore considered to hardly disturb such arrangement of group (2-1) as arranged densely on the surface of a substrate as mentioned above.

Group (2-4) does not have a hydrolyzable silyl group and is therefore considered to hardly disturb such arrangement of group (2-1) as arranged densely on the surface of a substrate as mentioned above.

Calculation of the respective proportions of groups (2-1) to (2-4) to the total of group $B^{10}$, is carried out by a method of identifying groups (2-1) to (2-4) by $^1$H-NMR (solvent: CDCl$_3$, internal standard: TMS (trimethylsilane)), whereupon the molar ratios of the respective groups are calculated.

That is, the molar ratios of the respective groups are calculated from ratios of those having the integrated intensities of the following portions identified by " " divided by the number of hydrogen atoms. With respect to group (2-4), its cis form and trans form are respectively identified, and the respective molar ratios are calculated.

—CH$_2$CH$_2$"CH$_2$"SiL$_m$R$_n$ (2-1).

—CH$_2$CH(SiL$_m$R$_n$)"CH$_3$" (2-2).

—CH$_2$CH="CH$_2$" (2-3).

—CH="CH"CH$_3$ (2-4).

L may, for example, be an alkoxy group, a halogen atom, an acyl group or an isocyanate group. The alkoxy group is preferably a C$_{1-4}$ alkoxy group.

L is preferably a C$_{1-4}$ alkoxy group or a halogen atom from the viewpoint of easy industrial production. As the halogen atom, a chlorine atom is particularly preferred.

L is preferably a C$_{1-4}$ alkoxy group, since outgassing will be less during coating, and compound (1) will be excellent in storage stability. When the alkoxy group is an ethoxy group, long-term storage stability of the compound (1) will be excellent. When the alkoxy group is a methoxy group, the reaction time after application to the substrate of the composition will be shortened.

m is preferably 2 or 3, particularly preferably 3. By the presence of a plurality of L in the molecule, it is considered that bonding to the surface of a substrate becomes stronger, and compounds (1) adjacent on the substrate surface are bonded to each other to form a strong surface-treated layer.

When m is at least 2, the plurality of L present in one molecule may be the same or different from one another. From the viewpoint of availability of raw material and production efficiency, they are preferably the same as one another.

In —SiL$_m$R$_n$, R is a monovalent hydrocarbon group. The monovalent hydrocarbon group may, for example, be an alkyl group, a cycloalkyl group, an alkenyl group or an allyl group.

R is particularly preferably a monovalent saturated hydrocarbon group. The number of carbon atoms in the monovalent saturated hydrocarbon group is preferably from 1 to 6, more preferably from 1 to 3, particularly preferably 1 or 2. R is, in view of simplicity in synthesis, preferably a C$_{1-6}$ alkyl group, more preferably a C$_{1-3}$ alkyl group, particularly preferably a C$_{1-2}$ alkyl group.

n is an integer of from 0 to 2, and m+n=3. n is preferably 0 or 1, particularly preferably 0. n being 0 or 1 means that m is 3 or 2, whereby, as mentioned above, compounds (1) may be bonded to one another to form a strong surface-treated layer.

—SiL$_m$R$_n$ may, for example, be —Si(OCH$_3$)$_3$, —SiCH$_3$(OCH$_3$)$_2$, —Si(OCH$_2$CH$_3$)$_3$, —SiCl$_3$, —Si(OCOCH$_3$)$_3$, or —Si(NCO)$_3$. From the viewpoint of handling efficiency in industrial production, —Si(OCH$_3$)$_3$ is preferred.

Group X

X is a divalent organic group having no CF$_2$O. X may, for example, be preferably a C$_{1-6}$ fluoroalkylene group or a C$_{1-6}$ alkylene group. From the viewpoint of easy production, a C$_{1-6}$ fluoroalkylene group having at least one hydrogen atom, is preferred, and a group represented by the following formula (6) is particularly preferred.

—(CF$_2$)$_a$CFX$^1$—CH$_2$— (6)

Here, in the formula (6), a is from 0 to 2, and X$^1$ is F or CF$_3$.

Group (6) may, for example, be —CF$_2$CH$_2$—, —CF$_2$CF$_2$CH$_2$—, —CF$_2$CF$_2$CF$_2$CH$_2$— or —CF(CF$_3$)CH$_2$—.

Group A

Group A is a C$_{1-20}$ perfluoroalkyl group or B$^{10}$. The C$_{1-20}$ perfluoroalkyl group is preferably a C$_{1-6}$ perfluoroalkyl group, particularly preferably a C$_{1-3}$ perfluoroalkyl group, since it is thereby possible to form a surface-treated surface which is further excellent in abrasion resistance, whereby the water/oil repellency is less likely to be lowered even by repeated abrasion, when the present composition is used for surface treatment of a substrate. The perfluoroalkyl group may be linear or branched, or may have a substituent group containing a ring structure.

A is preferably CF$_3$—, CF$_3$CF$_2$—, CF$_3$CF$_2$CF$_2$—, CF$_3$CF$_2$CF$_2$CF$_2$—, CF$_3$CF$_2$CF$_2$CF$_2$CF$_2$—, or CF$_3$CF$_2$CF$_2$CF$_2$CF$_2$CF$_2$—, particularly preferably CF$_3$—, CF$_3$CF$_2$—, or CF$_3$CF$_2$CF$_2$—.

Group Q

Group Q is a single bond, —CH$_2$—, —CHF—, -Q$^1$-CH$_2$—, -Q$^1$-CHF—, -Q$^1$-O—CH$_2$—, -Q$^1$-O—CHF—, -Q$^1$-

CH₂—O— or -Q¹-CHF—O—. Q¹ is a C$_{1-10}$ fluoroalkylene group, a C$_{2-10}$ fluoroalkylene group having an etheric oxygen atom between carbon-carbon atoms, a C$_{1-10}$ alkylene group, or a C$_{2-10}$ alkylene group having an etheric oxygen atom between carbon-carbon atoms.

The fluoroalkylene group may be a perfluoroalkylene group or a fluoroalkylene group having at least one hydrogen atom. From such a viewpoint that water/oil repellency of the surface-treated layer will be superior, a perfluoroalkylene group is preferred. From such a view point that solubility of the present composition in a liquid medium is superior, and aggregation of the present composition is suppressed in a coating liquid or during its application to the surface of a substrate, whereby it is possible to form a surface-treated layer excellent in uniformity, a fluoroalkylene group having at least one hydrogen atom is preferred.

When group A is a C$_{1-20}$ perfluoroalkyl group, group Q is preferably a single bond, —CH₂—, -Q¹-CH₂— or -Q¹-O—CH₂— from the viewpoint of production efficiency of compound (1).

Q¹ preferably has from 1 to 8 carbon atoms. Q¹ in -Q¹-CH₂— is, for example, preferably —CF₂—, —CF₂CF₂OCF₂— or —CF₂CF₂OCF₂CF₂OCF₂—. Q¹ in -Q¹-O—CH₂— is preferably —CHFCF₂—, —CF₂CF₂—O—CHFCF₂—, —CF₂CF₂OCF₂CF₂—O—CHFCF₂—, —CF(CF₃)CF₂—O—CHFCF₂— or —CF(CF₃)CF₂OCF(CF₃)CF₂—O—CHFCF₂—. Above all from the viewpoint of abrasion resistance, Q¹ is preferably —CF₂— or linear Q¹. The linear Q¹ is preferably —CHFCF₂—, —CF₂CF₂—O—CHFCF₂—, —CF₂CF₂OCF₂CF₂—O—CHFCF₂—, —CF₂CF₂OCF₂— or —CF₂CF₂0CF₂CF₂0CF₂—.

Group A-O-Q-

The following groups may be mentioned as specific examples of group A-O-Q- when group Q is a single bond.

CF₃—O—,
CF₃CF₂—O—,
CF₃CF₂CF₂—O—.

The following groups may be mentioned as specific examples of group A-O-Q- when group Q is -Q¹-O—CH₂—.

CF₃—O—CHFCF₂—O—CH₂—,
CF₃CF₂—O—CHFCF₂—O—CH₂—,
CF₃CF₂CF₂—O—CHFCF₂—O—CH₂—,
CF₃CF₂CF₂CF₂—O—CHFCF₂—O—CH₂—,
CF₃CF₂CF₂CF₂CF₂CF₂—O—CHFCF₂—O—CH₂—,
CF₃—O—CF₂CF₂—O—CHFCF₂—O—CH₂—,
CF₃CF₂—O—CF₂CF₂—O—CHFCF₂—O—CH₂—,
CF₃—O—CF₂CF₂OCF₂CF₂—O—CHFCF₂—O—CH₂—,
CF₃CF₂—O—CF₂CF₂OCF₂CF₂—O—CHFCF₂—O—CH₂—,
CF₃CF₂CF₂—O—CF(CF₃)CF₂—O—CHFCF₂—O—CH₂—,
CF₃CF₂CF₂—O—CF(CF₃)CF₂OCF(CF₃)CF₂—O—CHFCF₂—O—CH₂—.

The following groups may be mentioned as specific examples of group A-O-Q- when group Q is -Q¹-CH₂—.

CF₃—O—CF₂—CH₂—,
CF₃CF₂—O—CF₂—CH₂—,
CF₃—O—CF₂CF₂OCF₂—CH₂—,
CF₃CF₂—O—CF₂CF₂OCF₂—CH₂—,
CF₃—O—CF₂CF₂OCF₂OCF₂—CH₂—,
CF₃CF₂—O—CF₂CF₂OCF₂CF₂OCF₂—CH₂—.

The following groups may be mentioned as specific examples of group A-O-Q- when group Q is —CH₂—.

CF₃—O—CH₂—,
CF₃CF₂—O—CH₂—.

When group A is B¹⁰, group Q is preferably —CH₂— from viewpoint of production efficiency of compound (1). The following group may be mentioned as a specific example of group A-O-Q- in a case where Q is —CH₂—.

B¹⁰—O—CH₂—.

$$(C_bF_{2b}O)_d$$

In $(C_bF_{2b}O)_d$, b is an integer of from 1 to 10, and d is an integer of from 1 to 200, provided that when d is at least 2, $(C_bF_{2b}O)_d$ may be composed of at least two types of $C_bF_{2b}O$ different in b.

b is preferably an integer of from 1 to 4 with a view to sufficiently imparting abrasion resistance and fingerprint stain removability to the surface-treated layer, and b is preferably 1 or 2 with a view to sufficiently imparting lubricity to the surface-treated layer. Therefore, with a view to sufficiently imparting abrasion resistance, fingerprint stain removability and lubricity to the surface-treated layer, $(C_bF_{2b}O)_d$ wherein b is an integer of from 1 to 4, and $(C_bF_{2b}O)_d$ wherein b is 1 or 2, may be combined in such a combination that b is different.

In a case where b is at least 2, $C_bF_{2b}$ may be linear or branched. With a view to sufficiently imparting fingerprint stain removability and lubricity to the surface-treated layer, linear is preferred.

d is preferably an integer of at least 2, more preferably an integer of at least 10, particularly preferably an integer of at least 20, with a view to sufficiently imparting water/oil repellency to the surface-treated layer. If the number average molecular weight of compound (1) is too large, the number of hydrolyzable silyl groups present per unit molecular weight is decreased, and abrasion resistance of the surface-treated layer will be lowered, and from such a viewpoint, d is preferably an integer of at most 150, more preferably an integer of at most 100, particularly preferably an integer of at most 80.

When d is at least 2, $(C_bF_{2b}O)_d$ may be one composed of at least two types of $C_bF_{2b}O$ different in b.

In $(C_bF_{2b}O)_d$, when at least two types of $C_bF_{2b}O$ different in b are present, the binding order of respective $C_bF_{2b}O$ is not limited. For example, in a case where CF₂O and CF₂CF₂O are present, CF₂O and CF₂CF₂O may be randomly arranged, or CF₂O and CF₂CF₂O may be alternately arranged. Otherwise, a block composed of a plurality of CF₂O and a block composed of a plurality of CF₂CF₂O may be linked.

$(C_bF_{2b}O)$ may, for example, be (CF₂O), (C₂F₄O), (C₃F₆O), (C₄F₈O), (C₆F₁₀O) or the like. The combination of at least two types of $(C_bF_{2b}O)$ different in b may be any combination of at least two types among them. With a view to sufficiently imparting water/oil repellency, abrasion resistance, fingerprint stain removability to the surface-treated layer, groups represented by the following formulae (8-1) to (8-6) are preferred, and a group represented by the following formula (8-1), a group represented by the following formula (8-2), a group represented by the following formula (8-3) or a group represented by the following formula (8-5) is particularly preferred.

$$(CF_2CF_2O)_d \tag{8-1}$$

$$\{(CF_2CF_2O)_{d1}(CF_2CF_2CF_2CF_2O)_{d2}\} \tag{8-2}$$

$$\{(CF_2O)_{d1}(CF_2CF_2O)_{d2}\} \tag{8-3}$$

$(CF(CF_3)CF_2O)_d$ (8-4)

$(CF_2CF_2CF_2O)_d$ (8-5)

$\{(CF_2O)_{d1}(CF(CF_3)CF_2O)_{d2}\}$ (8-6)

Each of d1 and d2 is an integer of at least 1, provided that d1+d2 is an integer of from 2 to 200. Further, in group (8-2), the binding order of d1 number of $(CF_2CF_2O)$ and d2 number of $(CF_2CF_2CF_2CF_2O)$ is not limited. The same applies to group (8-3) and group (8-6).

Among them, $\{(CF_2O)_{d1}(CF_2CF_2O)_{d2}\}$ is preferably $CF_2O\{(CF_2O)_{d1-1}(CF_2CF_2O)_{d2}\}$ (wherein the left hand side $CF_2O$ is bonded to Q in the formula (1)) from the viewpoint of production efficiency of the present composition.

With a view to sufficiently imparting water/oil repellency, abrasion resistance and fingerprint stain removability to the surface-treated layer, d1 is preferably an integer of at least 2, more preferably an integer of at least 5, particularly preferably an integer of at least 10. If the number average molecular weight of compound (1) is too large, the number of hydrolyzable silyl groups present per unit molecular weight is decreased, and abrasion resistance of the surface treated layer is lowered, and from such a viewpoint, d1 is preferably an integer of at most 100, more preferably an integer of at most 80, particularly preferably an integer of at most 50.

With a view to sufficiently imparting water/oil repellency, abrasion resistance and fingerprint stain removability to the surface-treated layer, d2 is preferably an integer of at least 2, more preferably an integer of at least 5, particularly preferably an integer of at least 10. If the number average molecular weight of compound (1) is too large, the number of hydrolyzable silyl groups present per unit molecular weight is decreased, and abrasion resistance of the surface treated layer is lowered, and from such a viewpoint, d2 is preferably an integer of at most 100, more preferably an integer of at most 80, particularly preferably an integer of at most 50.

Compound (1) can be produced as a mixture of plural types of compounds different in the number of d in $(C_bF_{2b}O)_d$. In such a case, the average value of d as the mixture is preferably from 1 to 200, particularly preferably from 2 to 150. Further, compound (1) can be produced as a mixture of plural types of compounds different in the numbers of d1 and d2. In such a case, the average value of d1 as the mixture is preferably from 1 to 100, and the average value of d2 is preferably from 1 to 100.

Preferred Embodiment of Compound (1)

As compound (1) wherein A is a perfluoroalkyl group, the following compounds are preferred.

When Q is a single bond, the following compounds (111) to (113) may be mentioned.

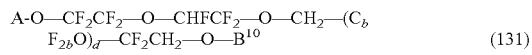  (111)

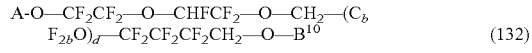  (112)

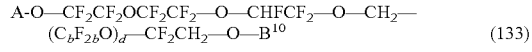  (113)

When Q is $-Q^1-O-CH_2-$, the following compounds (121) to (122) and compounds (131) to (138) may be mentioned.

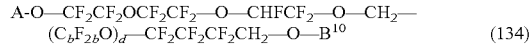  (121)

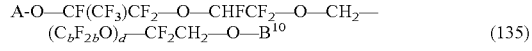  (122)

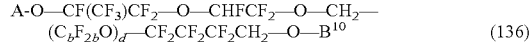  (131)

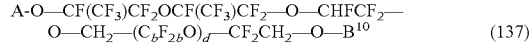  (132)

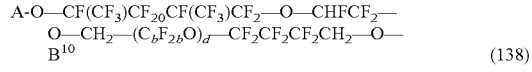  (133)

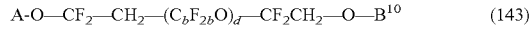  (134)

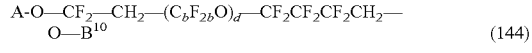  (135)

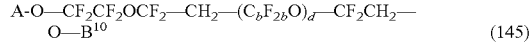  (136)

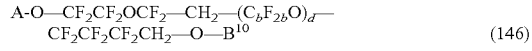  (137)

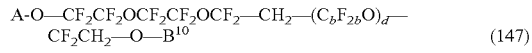  (138)

When Q is $-Q^1-CH_2-$, the following compounds (143) to (148) may be mentioned.

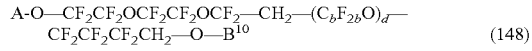  (143)

(144)

(145)

(146)

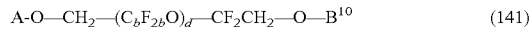  (147)

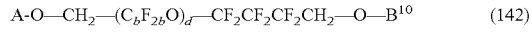  (148)

When Q is $-CH_2-$, the following compounds (141) and (142) may be mentioned.

(141)

(142)

As compound (1) wherein A is $B^{10}$, the following compounds (151) to (153) wherein Q is $-CH_2-$, may be mentioned.

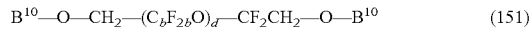  (151)

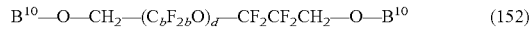  (152)

  (153)

Molecular Weights

The molecular weight of compound (1) is preferably from 1,000 to 10,000, particularly preferably from 1,500 to 10,000. When the molecular weight is within the above range, it is possible to obtain a surface-treated layer excellent in abrasion resistance, whereby the performance is less likely to be lowered even by repeated abrasion.

The number average molecular weight (Mn) of the present composition is preferably from 1,000 to 10,000, particularly preferably from 1,500 to 10,000. When the number average molecular weight (Mn) is in the above range, it is possible to obtain a surface-treated layer excellent in abrasion resistance, whereby the performance is less likely to be lowered even by repeated abrasion.

The number average molecular weight (Mn) of the present composition is a value obtained by the following method by means of a NMR analytical method. That is, by $^{19}$F-NMR (solvent: $CDCl_3$, internal standard: $CFCl_3$), the repeating units of $(C_bF_{2b}O)_d$ are identified, and at the same time, the number of repeating units are calculated, to calculate an average value of the molecular weight of $(C_bF_{2b}O)_d$ per molecule. Then, by $^1$H-NMR (solvent: $CDCl_3$, internal standard: TMS), identification and quantification of A and $B^{10}$ being terminal groups, are conducted, and based on the number of moles of the terminal groups, the number average molecular weight (Mn) of the present composition is calculated.

[Method for Producing Fluorinated Ether Composition]

The present composition can be produced by a method having a step of reacting a compound represented by the following formula (3) and a compound represented by the following formula (4), in the presence of a transition metal catalyst (C) and at least one compound (D) selected from the group consisting of nitrogen-containing compounds and sulfur-containing compounds. The hydrosilylation reaction may be carried out in the presence or absence of a solvent.

$$A^1\text{-O-Q-}(C_bF_{2b}O)_d\text{—X—O—}B^{20} \qquad (3)$$

$$HSiL^1_mR_n \qquad (4)$$

The symbols in the formulae (3) and (4) represent the following.

$A^1$: the same $C_{1-20}$ perfluoroalkyl group as A in the above formula (1) or the following $B^{20}$.

Q: the same group as Q in the above formula (1).

b, d: the same numerical values as b and d in the above formula (1), respectively.

X: the same group as X in the above formula (1).

$B^{20}$: a group represented by the above formula (2-3).

$L^1$: a hydrolyzable group.

R: the same group as R in the above formula (1).

m and n: the same numerical values as m and n in the above formula (1), respectively.

$(C_bF_{2b}O)_d$ in the formula (3) being the same group as $(C_bF_{2b}O)_d$ in the formula (1) means that $(C_bF_{2b}O)_d$ does not change in the process for producing the present composition by using said compound (3). The same applies to $A^1$ in the formula (3) and R in the formula (4).

Here, in a case where compound (3) is high molecular weight material having many repeating units in $(C_bF_{2b}O)_d$, such compound (3) may be a group of compounds having a molecular weight distribution, but even in such a case, such compound (3) is regarded to be substantially one type of compound. Therefore, in compound (1) as the reaction product, even if it has a molecular weight distribution due to $(C_bF_{2b}O)_d$, such compound shall be regarded as one type of compound.

Compound (3)

Compound (3) can be obtained by the method of allylating a hydroxy group in a fluorinated ether compound having the hydroxy group at a terminal by using e.g. $D\text{-}CH_2CH\text{=}CH_2$ thereby to introduce group (2-3) at the terminal. D is a leaving group and is, for example, a halogen atom such I, Br or Cl.

The fluorinated ether compound having a hydroxy group at a terminal can be produced by a known method, depending on the structure of $(C_bF_{2b}O)_d$, etc. For example, a method for production by using, as a starting material, a commercially available polyoxyalkylene compound or a compound having poly(oxyperfluoroalkylene) chains; or a method for production by using, as a starting material, a compound commercially available as an intermediate for the preparation of a perfluoropolyether compound, may be mentioned. Further, the fluorinated ether compound having a hydroxy group at a terminal is also available as a commercial product.

Specific examples for the production method of compound (3) will be described below.

Method 1

For example, in a case where $A^1$ is a perfluoroalkyl group, a compound represented by the following formula (321) can be prepared by the following method.

$$A^1\text{-O—CHFCF}_2\text{—O—CH}_2\text{—CF}_2O\{(CF_2O)_{d1\text{-}1} \\ (CF_2CF_2O)_{d2}\}\text{—CF}_2CH_2\text{—O—CH}_2CH\text{=}CH_2 \qquad (321)$$

Firstly, in the presence of a basic compound, a compound represented by the following formula (321a) is reacted with $A^1\text{-O—CF=CF}_2$, to obtain a mixture of a compound represented by the following formula (321b), a compound represented by the following formula (321c) and unreacted compound (321a).

$$HO\text{—CH}_2\text{—CF}_2O\{(CF_2O)_{d1\text{-}1}(CF_2CF_2O)_{d2}\}\text{—} \\ CF_2CH_2\text{—OH} \qquad (321a)$$

$$A^1\text{-O—CHFCF}_2\text{—O—CH}_2\text{—CF}_2O\{(CF_2O)_{d1\text{-}1} \\ (CF_2CF_2O)_{d2}\}\text{—CF}_2CH_2\text{—OH} \qquad (321b)$$

$$A^1\text{-O—CHFCF}_2\text{—O—CH}_2\text{—CF}_2O\{(CF_{20})_{d1\text{-}1} \\ (CF_2CF_2O)_{d2}\}\text{—CF}_2CH_2\text{—O—CF}_2CHF\text{—O-}A^1 \qquad (321c)$$

Then, from the mixture, compound (321b) is isolated, and in the presence of a basic compound, compound (321b) is reacted with $D\text{-}CH_2CH\text{=}CH_2$, to obtain compound (321).

$$A^1\text{-O—CHFCF}_2\text{—O—CH}_2\text{—CF}_2O\{(CF_2O)_{d1\text{-}1} \\ (CF_2CF_2O)_{d2}\}\text{—CF}_2CH_2\text{—O—CH}_2CH\text{=}CH_2 \qquad (321)$$

Method 2

For example, in a case where $A^1$ is a perfluoroalkyl group, a compound represented by the following formula (311) can be prepared by the following method.

$$A^1\text{—O—}(CF_2CF_2O)_d\text{—CF}_2CH_2O\text{—CH}_2CH\text{=}CH_2 \qquad (311)$$

Firstly, a compound represented by the following formula (311a) is reacted and esterified with $R^{F2}C(\text{=}O)F$ to obtain a compound represented by the following formula (311b).

$$R^{H1}\text{—O—}(CH_2CH_2O)_d\text{—CH}_2CH_2OH \qquad (311a)$$

$$R^{H1}\text{—O—}(CH_2CH_2O)_d\text{—CH}_2CH_2OC(\text{=}O)R^{F2} \qquad (311b)$$

Here, $R^{H1}$ is an alkyl group, and $R^{F2}$ is a perfluoroalkyl group which may have an etheric oxygen atom between carbon-carbon atoms.

Then, compound (311b) is perfluorinated to obtain compound (311c). The perfluorination method may, for example, be a liquid phase fluorination method, wherein fluorine gas is introduced into a liquid phase for reaction. Group $A^1$ is formed as the hydrogen atoms of $R^{H1}$ are substituted with fluorine atoms.

$$A^1\text{—O—}(CF_2CF_2O)_d\text{—CF}_2CF_2OC(\text{=}O)R^{F2} \qquad (311c)$$

Then, by a decomposition reaction of the ester bond of compound (311c), a compound of the following formula (311d) is obtained.

$$A^1\text{—O—}(CF_2CF_2O)_d\text{—CF}_2C(\text{=}O)F \qquad (311d)$$

Then, compound (311d) and $R^{H2}OH$ are subjected to an esterification reaction, to obtain a compound represented by the following formula (311e). The esterification reaction may be carried out by a known method (for example, a method disclosed in U.S. Pat. No. 3,810,874). Compound (311e) may also be obtained by a method of reacting compound (311c) and $R^{H2}OH$.

$$A^1\text{-}O\text{---}(CF_2CF_2O)_d\text{---}CF_2C(=O)OR^{H2} \quad (311e)$$

Here, $R^{H2}$ represents an alkyl group.

Then, by a reduction reaction of compound (311e), compound (311f) is obtained, and by reacting $D\text{-}CH_2CH=CH_2$ to the hydroxy group of compound (311f) for allylation, compound (311) is obtained. The reduction reaction can be carried out by a known method disclosed in e.g. paragraphs [0021] of JP-A-10-72568. The reduction reaction is preferably carried out by using a reducing agent such as $NaBH_4$, $BH_3$-THF or $LiAlH_4$.

$$A^1\text{-}O\text{---}(CF_2CF_2O)_d\text{---}CF_2CH_2OH \quad (311f)$$

Method 3

For example, in a case where $A^1$ is group $B^{20}$, a compound represented by the following formula (341) can be prepared in the same process as the above method (2) by using, as a starting material, a compound having hydroxy groups at both terminals represented by the following formula (341a). That is, it can be prepared by sequentially carrying out esterification of hydroxy groups at both terminals of the compound, perfluorination by fluorine gas, a decomposition reaction of the ester bond, esterification with $R^{H2}OH$, a reduction reaction and allylation.

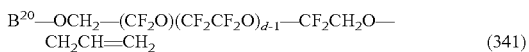
$$B^{20}\text{---}OCH_2\text{---}(CF_2O)(CF_2CF_2O)_{d\text{-}1}\text{---}CF_2CH_2O\text{---}\\CH_2CH=CH_2 \quad (341)$$

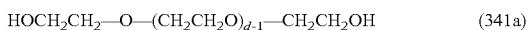
$$HOCH_2CH_2\text{---}O\text{---}(CH_2CH_2O)_{d\text{-}1}\text{---}CH_2CH_2OH \quad (341a)$$

Compound (4)

$L^1$ in compound (4) may be a group of the same type as, or different type from, L in the compound (1), and in a case where it is a group of different type, $L^1$ is a halogen atom.

That is, in a case where L in compound (1) is an alkoxy group, it is possible to produce the desired compound (1) by a method of reacting compound (3) and compound (4) wherein $L^1$ is a halogen atom for hydrosilylation, and then, replacing the halogen atom with an alkoxy group. The halogen atom is preferably a chlorine atom. As the method for replacing the halogen atom with an alkoxy group, a known method may be used. For example, in a case where the halogen atom is a chlorine atom, it is possible to replace the chlorine atom with an alkoxy group by a method of reacting an orthoformic acid trialkyl ester such as methyl orthoformate to convert the chlorine atom to an alkoxy group; or a method of reacting an alkali metal alkoxide such as sodium methoxide to convert the chlorine atom to an alkoxy group.

The molar ratio of compound (4) to group $B^{20}$ of compound (3) is preferably from 0.95 to 20, particularly preferably from 0.98 to 5. When it is at least the lower limit value in the above range, the present composition wherein the proportions of groups (2-1) to (2-4) are within the specific ranges, can easily be obtained. Further, the reaction rate of the hydrosilylation reaction is excellent. When it is at most the upper limit value in the above range, it is possible to obtain the present composition while suppressing the amount of compound (4) to be used.

Transition Metal Catalyst (C)

As the transition metal catalyst (C), Groups 8 to 10 transition metal catalysts are preferred, and among them, a platinum (Pt) catalyst, a ruthenium (Ru) catalyst, a rhodium (Rh) catalyst, etc. may be mentioned. A platinum catalyst is preferred, since by combination with the after-described compound (D), the present composition wherein groups (2-1) to (2-4) are within the specific ranges can thereby be more easily obtained. Here, Groups 8 to 10 are group numbers by IUPAC Inorganic Chemical Nomenclature Revised Edition (1989).

The platinum catalyst may, for example, be a Pt/divinyltetramethyldisiloxane complex, a Pt/tetramethyltetravinylcyclotetrasiloxane complex, chloroplatinic acid or platinum oxide. Among them, either one of a Pt/divinyltetramethyldisiloxane complex and a Pt/tetramethyltetravinylcyclotetrasiloxane complex is particularly preferred, since by combining with the after-described compound (D), the present composition wherein groups (2-1) to (2-4) are within the specific ranges can thereby be more easily obtained.

As the amount of the transition metal catalyst (C) to be used, the mass ratio to compound (3) is preferably from 0.1 to 1,000 ppm, particularly preferably from 1 to 100 ppm. Within the above range, the reaction proceeds under proper reaction conditions, and there will be less coloration due to the catalyst.

Compound (D)

Among compounds (D), the nitrogen-containing compounds may, for example, be an aliphatic amine compound (diethylamine (hereinafter referred to also as "DEA"), a triethylamine (hereinafter referred to also as "TEA") or the like), an aromatic amine compound (aniline, pyridine or the like), an amide phosphate (hexamethylphosphoramide (hereinafter referred to also as "HMPA") or the like), an amide compound (N,N-diethylacetamide, N,N-diethylformamide, N,N-dimethylacetamide (hereinafter referred to also as "DMAc"), N-methylformamide (hereinafter referred to also as "NMF"), N,N-dimethylformamide (hereinafter referred to also as "DMF") or the like), a urea compound (tetramethyl urea or the like), a cyclic amide compound (N-methylpyrrolidone (hereinafter referred to also as "NMP") or the like), etc. Among the nitrogen-containing compounds, the after-described compounds having higher donor number are preferred, and an aliphatic amine compound, an aromatic amine compound, an amide phosphoric acid or a urea compound is preferred. Further, if the basicity of the nitrogen-containing compounds is high, side reactions such as hydrolysis and condensation reaction of the hydrolyzable group tend to proceed, and therefore, the basicity should better be low or a neutral compound is preferred. From such a viewpoint, an aromatic amine compound, an amide phosphoric acid or a urea compound is preferred.

Among compounds (D), the sulfur-containing compounds may, for example, be a sulfoxide compound (tetramethylene sulfoxide (hereinafter referred to also as "TMSO"), dimethyl sulfoxide (hereinafter referred to also as "DMSO") or the like), etc.

Compounds (D) may be used alone, or two or more of them may be used in combination.

As compound (D), at least one type of an aromatic amine compound and a sulfoxide compound is preferred, and at least one type of TMSO and DMSO is particularly preferred, since by combination with the transition metal catalyst (C), the present composition wherein the proportions of groups (2-1) and (2-4) are within the specific ranges, can thereby be more easily obtained.

Each of the above nitrogen-containing compounds and sulfur-containing compounds exemplified as compound (D) has a large donor number. The donor number is one of solvent parameters and an index for electron (pair) donating ability. The larger the donor number, the larger the electron (pair) donating ability, and the higher the coordination ability. When compound (D) having a large donor number is used in combination with the transition metal catalyst (C), such compound (D) is coordinated with a transition metal in the transition metal catalyst (C), whereby coordination of compound (3) with the transition metal is considered to be controlled. As a result, it is considered possible to more readily obtain the present composition wherein the proportions of groups (2-1) to (2-4) are within the specific ranges.

The donor number is the amount of heat when compound (D) and $SbCl_5$ form a 1:1 adduct, and the donor numbers of various compounds, a calculation method for the donor number, etc. are disclosed, for example, in the following reference literatures (1) and (2). (1) Pure & Appl. Chem., Vol. 41, No. 3, pp. 291-326, 1975. (2) Pure & Appl. Chem., Vol. 58, No. 8, pp. 1153-1161, 1986.

The amount of compound (D) to be used, is preferably 0.001 to 1,000 parts by mass, particularly preferably from 0.01 to 10 parts by mass, to 100 parts by mass of compound (3). Within the above range, the present composition wherein the proportions of groups (2-1) to (2-4) are within the specific ranges can be more easily obtained.

The mass ratio in amount of compound (D) to transition metal catalyst (C) to be used (i.e. compound (D):transition metal catalyst (C)) is preferably from 10:1 to 10,000:1, particularly preferably from 20:1 to 1,000:1. Within the above range, the present composition wherein the proportions of groups (2-1) to (2-4) are within the specific ranges can be more easily obtained.

Solvent

In a case where the hydrosilylation reaction is conducted in the presence of a solvent, as the solvent, an organic solvent is preferred. The organic solvent may be a fluorinated organic solvent or a non-fluorinated organic solvent, or both solvents may be used.

The fluorinated organic solvent may, for example, be a fluorinated alkane, a fluorinated aromatic compound, a fluoroalkyl ether, a fluorinated alkylamine or a fluoroalcohol.

As the fluorinated alkane, a compound having 4 to 8 carbon atoms is preferred. Commercial products may, for example, be $C_6F_{13}H$ (AC-2000: trade name, manufactured by Asahi Glass Company, Limited), $C_6F_{13}C_2H_5$ (AC-6000: trade name, manufactured by Asahi Glass Company, Limited), $C_2F_5CHFCHFCF_3$ (Vertrel: trade name, manufactured by DuPont), etc.

The fluorinated aromatic compound may, for example, be hexafluorobenzene, trifluoromethylbenzene, perfluorotoluene, 1,3-bis(trifluoromethyl) benzene or 1,4-bis (trifluoromethyl)benzene.

As the fluoroalkyl ether, a compound having from 4 to 12 carbon atoms is preferred. Commercial products may, for example, be $CF_3CH_2OCF_2CF_2H$ (AE-3000: trade name, manufactured by Asahi Glass Company, Limited), $C_4F_9OCH_3$ (Novec-7100: trade name, 3M Company), $C_4F_9OC_2H_5$ (Novec-7200: trade name, manufactured by 3M Company), $C_6F_{13}OCH_3$ (Novec-7300: trade name, manufactured by 3M Company), etc.

The fluorinated alkyl amine may, for example, be perfluorotripropylamine or perfluorotributylamine.

The fluoroalcohol may, for example, be 2,2,3,3-tetrafluoropropanol, 2,2,2-trifluoroethanol or hexafluoroisopropanol.

As the fluorinated organic solvent, it is preferred to use at least one organic solvent (E) selected from the group consisting of fluorinated alkanes, fluorinated aromatic compounds and fluoroalkyl ethers, from the viewpoint of compatibility with other compounds.

As the non-fluorinated organic solvent, a compound composed solely of hydrogen atoms and carbon atoms, or a compound composed solely of hydrogen atoms, carbon atoms and oxygen atoms, is preferred, and a hydrocarbon-type organic solvent, a ketone-type organic solvent, an ether-type organic solvent, or an ester-type organic solvent, may be mentioned.

The hydrocarbon-type organic solvent may, for example, be preferably hexane, heptane or cyclohexane.

The ketone-type organic solvent may, for example, be preferably acetone, methyl ethyl ketone, or methyl isobutyl ketone.

The ether-type organic solvent may, for example, be preferably diethyl ether, tetrahydrofuran, or ethylene glycol dimethyl ether.

The ester-type organic solvent may, for example, be preferably ethyl acetate, or butyl acetate.

As the non-fluorinated organic solvent, a hydrocarbon-type organic solvent is particularly preferred from the viewpoint of compatibility of compound (3) with other compounds, etc.

As the amount of the solvent to be used, the mass ratio to 100 parts by mass of compound (3) is preferably from 0.1 to 10,000 parts by mass, particularly preferably from 1 to 1,000 parts by mass. Within the above range, there will be an effect to let respective compounds be compatibilized with one another, and the reaction conditions may be made mild.

Reaction Conditions

The reaction of compound (3) and compound (4) is carried out by using, for example, a container made of a resin such as a polyolefin or a fluororesin, a glass container, a container made of metal such as SUS, or a lined container coated with a fluorinated resin.

The reaction temperature is preferably from 0 to 100° C., particularly preferably from 20 to 50° C., whereby the reaction proceeds sufficiently and formation of by-products is suppressed. The reaction time is preferably from 1 to 100 hours, particularly preferably from 2 to 20 hours. The reaction pressure is preferably from −0.01 to 1 MPaG, more preferably from 0 to 0.1 MPaG. "G" in "MPaG" represents the gauge pressure.

[Coating Liquid]

The coating liquid of the present invention (hereinafter referred to also as "the present coating liquid") comprises the present composition and a liquid medium. The present coating liquid may be any liquid, i.e. may be a solution or a dispersion.

The present coating liquid may simply contain the present composition and may also contain impurities such as by-products formed during the production process of the present composition. Further, as the present composition to be contained in the coating liquid, some of compound (1) in the present composition may be contained in such a state that their hydrolyzable silyl groups are partially hydrolyzed, and further may be contained in such a state that silanol groups formed by the hydrolysis reaction are partially condensed.

The concentration of the present composition is preferably from 0.001 to 10 mass %, particularly preferably from 0.01 to 1 mass %, in the present coating liquid.

Liquid Medium

As the liquid medium, for example, one or more of the previously exemplified fluorinated organic solvents and non-fluorinated organic solvents may be used.

The liquid medium is preferably at least one organic solvent selected from the group consisting of a fluorinated alkane, a fluorinated aromatic compound, a fluoroalkyl ether, a compound composed solely of hydrogen atoms and carbon atoms, and a compound composed solely of hydrogen atoms, carbon atoms and oxygen atoms. In particular, the above mentioned fluorinated organic solvent (E) is preferred.

As the liquid medium, it is preferred to contain at least one organic solvent selected from the group consisting of a fluorinated alkane, a fluorinated aromatic compound, a fluoroalkyl ether, as fluorinated organic solvents, and a compound composed solely of hydrogen atoms, carbon atoms and oxygen atoms, as a non-fluorinated solvent, in an amount in total of at least 90 mass % of the entire liquid medium, with a view to increasing the solubility of the present composition.

The coating liquid preferably contains the liquid medium in an amount of from 90 to 99.999 mass %, particularly preferably from 99 to 99.9%.

The present coating liquid may contain, in addition to the present composition and the liquid medium, other components in a range not to impair the effects of the present invention.

Such other components may, for example, be known additives such as an acid catalyst, a basic catalyst, etc. for promoting hydrolysis and condensation reactions of hydrolyzable silyl groups.

The acid catalyst may, for example, be hydrochloric acid, nitric acid, acetic acid, sulfuric acid, phosphoric acid, sulfonic acid, methanesulfonic acid or p-toluenesulfonic acid.

The basic catalyst may, for example, be sodium hydroxide, potassium hydroxide, or ammonia.

In the present coating liquid, the content of other components is preferably at most 10 mass %, particularly preferably at most 1 mass %.

The solid content concentration of the present coating liquid is preferably from 0.001 to 10 mass %, particularly preferably from 0.01 to 1 mass %. The solid content concentration of the coating liquid is a value calculated from the mass of the coating liquid prior to heating and the mass after heating for 4 hours in a convection dryer at 120° C. Further, the concentration of the present composition can be calculated from the solid content concentration and the charged amounts of the present composition, the solvent, etc.

[Substrate having Surface-Treated Layer]

The substrate having a surface-treated layer of the invention has a surface-treated layer formed from the present composition.

Surface-Treated Layer

The surface-treated layer is formed by forming a layer of the present composition on the surface of a substrate and at the same time, hydrolyzing hydrolyzable silyl groups ($—SiL_mR_n$) of compound (1) and reacting silanol groups thereby formed, to e.g. reactive groups on the substrate surface. It is considered that in the surface-treated layer, formed silanol groups will be reacted with and bonded to silanol groups, hydroxy groups or other reactive groups on the substrate surface, whereby compound (1) will be bonded to the substrate surface, and molecules of compound (1) will be mutually bonded by an intermolecular condensation reaction between silanol groups of compound (1). It is considered that by such reactions, excellent water/oil-repellency is imparted to the surface of the substrate, and at the same time, a surface-treated layer is formed which is excellent in abrasion resistance, whereby the water/oil repellency is less likely to be lowered even by repeated abrasion.

Substrate

The substrate in the present invention is not particularly limited so long as it is a substrate which is desired to have water/oil repellency imparted. The material for the substrate may, for example, be metal, resin, glass, ceramics, stone or a composite material thereof.

Touch Panel

By forming a surface-treated layer from the present composition, excellent initial water/oil repellency is imparted, and at the same time, it is possible to obtain excellent abrasion resistance whereby the water/oil repellency is less likely to be lowered even by repeatedly abrasion, performance (fingerprint stain removability) whereby fingerprint stains on the surface can be easily removed, smoothness (lubricity) when the surface is touched with a finger, and uniformity of the surface-treated layer (transparency, smoothness, less irregularity). Therefore, in the substrate having a surface-treated layer thus obtainable, the surface-treated layer has an excellent initial water/oil repellency and at the same time has excellent abrasion resistance, fingerprint stain removability, lubricity and uniformity, and thus, it is suitable as a member constituting a touch panel. The touch panel means an input device in an input/display device (touch panel device) having a display device and a device to input the contact position information by contact with a finger, etc. combined. The touch panel is constituted by a substrate and, depending upon the input detection method, a transparent conductive film, electrodes, wires, IC, etc. By using the side having the surface-treated layer of the substrate as the input surface of a touch panel, it is possible to obtain a touch panel wherein the surface-treated layer has excellent abrasion resistance, fingerprint stain removability, lubricity and uniformity.

The material for the touch panel substrate is light-transmitting. Here "is light-transmitting" means that the vertical incidence type visible light transmittance in accordance with JIS R3106 is at least 25%.

The material for the touch panel substrate is preferably glass or transparent resin. The glass may, for example, be preferably soda lime glass, alkali aluminosilicate glass, borosilicate glass, alkali-free glass, crystal glass or quartz glass, and chemically strengthened soda lime glass, chemically strengthened alkali aluminosilicate glass, or chemically strengthened borosilicate glass is particularly preferred. As the transparent resin, an acrylic resin or a polycarbonate is preferred.

Further, the substrate in the present invention is useful also as a display substrate constituting the outer-most surface of various displays, such as a liquid crystal display, a CRT display, a projection display, a plasma display, an EL display, etc. and by forming a surface-treated layer by surface treatment using the present composition or the present coating liquid, it is possible to obtain a display wherein the surface-treated layer has excellent abrasion resistance, fingerprint stain removability, lubricity and uniformity.

[Method for Producing Substrate having Surface-Treated Layer]

Dry Coating Method

The present composition is useful, as it is, for a method for producing a substrate having a surface-treated layer by treating the surface of a substrate by a dry coating method. The present composition is suitable for forming a surface-treated layer having excellent adhesion by a dry coating method. As the dry coating method, a method such as vacuum vapor deposition, CVD or sputtering may be mentioned. With a view to suppressing decomposition of compound (1) contained in the present composition and from the viewpoint of simplicity of apparatus, a vacuum vapor deposition method can be suitably used. The vacuum vapor evaporation method may be subdivided into e.g. a resistance heating method, an electron beam heating method, a high frequency induction heating method, a reactive vapor deposition method, a molecular beam epitaxy method, a hot wall vapor deposition method, an ion plating method and a cluster ion beam method, and any method may be used. With a view to suppressing decomposition of compound (1) contained in the present composition and from the viewpoint of simplicity of apparatus, a resistance heating method can be suitably used. The vacuum vapor deposition apparatus is not particularly limited, and a known apparatus can be used.

Film forming conditions in the case of using a vacuum vapor deposition method may vary depending on the type of the vacuum vapor deposition method to be employed, and in the case of a resistance heating method, the vacuum degree before deposition is preferably at most $1\times10^{-2}$ Pa, particularly preferably at most $1\times10^{-3}$ Pa. The heating temperature of the deposition source is not particularly limited so long as it is a temperature at which the deposition source of the present composition has a sufficient vapor pressure. Specifically, it is preferably from 30 to 400° C., particularly preferably from 50 to 300° C. When the heating temperature is at least the lower limit value in the above range, the deposition rate will be improved. When it is at most the upper limit value in the above range, it is possible to impart the initial water/oil-repellency, abrasion resistance and fingerprint stain removability to the surface of a substrate, without causing decomposition of compound (1). A the time of vacuum vapor deposition, the substrate temperature is preferably within a range of from room temperature to 200° C. When the substrate temperature is at most 200° C., the deposition rate will be good. The upper limit of the substrate temperature is more preferably at most 150° C., particularly preferably at most 100° C.

In the case of treating the surface of a substrate by a dry coating method using the present composition, the surface-treated layer to be formed on the surface of the substrate by such treatment, is preferably from 1 to 100 nm, particularly preferably from 1 to 50 nm in its film thickness. When the film thickness of the surface-treated layer is at least the lower limit value in the above range, the effect by the surface treatment is likely to be sufficiently obtained. When it is at most the upper limit value in the above range, utilization efficiency will be high. Here, for the film thickness, for example, by using X-ray diffractometer ATX-G (manufactured by Rigaku Corporation) for thin film analysis, an interference pattern of reflected X-ray is obtained by an X-ray reflectance method, and the film thickness is calculated from the oscillation period of the interference pattern.

In particular, in the vacuum vapor deposition method, it is possible to form a surface-treated layer which has a large content of compound (1) and a less content of impurities, and which is further excellent in the initial water/oil-repellency, abrasion resistance and fingerprint stain resistance. This is considered to be such that according to the vacuum vapor deposition method, by-products with low vapor pressures tend to be vapor deposited to the surface of a substrate prior to compound (1), and as a result, it is possible to suppress a phenomenon of preventing chemical bonding between the surface of a substrate and compound (1) responsible for development of the performance.

Wet Coating Method

By applying the present coating liquid on the surface of a substrate, followed by drying, it is possible to produce a substrate having a surface-treated layer.

As the method for applying the coating liquid, a known technique may suitably be used.

As the coating method, preferred is a spin coating method, a wipe coating method, a spray coating method, a squeegee coating method, a dip coating method, a die coating method, an ink-jet method, a flow coating method, a roll coating method, a casting method, a Langmuir-Blodgett method or a gravure coating method.

The method of drying may be any method so long as the liquid medium can be thereby dried and removed, and a known technique may suitably be used. The drying temperature is preferably from 10 to 300° C., particularly preferably from 20 to 200° C.

The surface-treated layer formed on the surface of a substrate after drying and removing the liquid medium, is preferably from 1 to 100 nm, particularly preferably from 1 to 50 nm, in its film thickness. When the film thickness of the surface-treated layer is at least the lower limit value in the above range, the effect by the surface treatment is likely to be sufficiently obtained. When it is at most the upper limit value in the above range, utilization efficiency will be high. The measurement of the film thickness can be carried out in the same manner as the method of measuring the film thickness of the surface-treated layer to be formed by a dry coating method.

Post Treatment

After forming a surface-treated layer on the substrate surface by the dry coating method or wet coating method, in order to improve the durability against the abrasion of the surface-treated layer, if necessary, an operation for promoting the reaction between compound (1) and the substrate may be carried out. As such an operation, heating, humidification or light irradiation may, for example, be mentioned. For example, by heating a substrate having a surface-treated layer formed, in an atmosphere having moisture, it is possible to accelerate a reaction such as hydrolysis of hydrolyzable silyl groups to silanol groups, a reaction of the silanol groups and hydroxy groups on the substrate surface, or formation of a siloxane bond by a condensation reaction of silanol groups.

After the surface treatment, even a compound in the surface-treated layer may be removed as the case requires, so long as it is a compound not chemically bonded to another compound or the substrate. As a specific method, for example, a method of flowing a solvent on the surface-treated layer, or a method of wiping with a cloth impregnated with a solvent, may be mentioned.

EXAMPLES

Now, the present invention will be described in further detail with reference to Examples, but the present invention is not limited to these Examples.

Hereinafter, "%" is "mass %" unless otherwise specified.
Ex. 1 to 13, 23, 26, 33 and 36 are Examples of the present invention, and Ex. 21, 22, 24, 25, 27, 31, 32, 34, 35 and 37 are Comparative Examples.

Hereinafter, fluorinated organic solvent $C_6F_{13}H$ will be referred to as "AC-2000" (trade name, manufactured by Asahi Glass Company, Limited), and fluorinated organic solvent $C_6F_{13}C_2H_5$ will be referred to as "AC-6000" (trade name, manufactured by Asahi Glass Company, Limited).

Production Example 1: Production of Compound (3-1)

The following compound (3-1a) was obtained by the method in Ex. 1 in WO2009/008380.

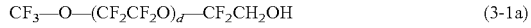

$$CF_3—O—(CF_2CF_2O)_d—CF_2CH_2OH \quad (3\text{-}1a)$$

NMR spectrum of compound (3-1a);
$^1$H-NMR (300.4 MHz, solvent: CDCl$_3$, standard: TMS) δ (ppm): 1.9 (1H), 3.9 (2H).
$^{19}$F-NMR (282.7 MHz, solvent: CDCl$_3$, standard: CFCl$_3$) δ (ppm): −56.2 (3F), −81.4 (2F), −89.5 (26F), −91.4 (2F).
The average value of the number of units d: 7.
The number average molecular weight: 1,000.

In a two-necked eggplant flask of 200 mL, 50.0 g of compound (3-1a), 2.1 g of tetrabutylammonium hydrogen sulfate, 18.0 g of allyl bromide and 26.4 g of a 30% aqueous sodium hydroxide solution were added and stirred at 60° C. for 8 hours. After completion of the reaction, 50 g of AC-2000 was added, followed by washing once with a dilute aqueous hydrochloric acid solution to recover the organic phase. The recovered organic phase was passed through a silica gel column, and the recovered solution was concentrated by an evaporator to obtain 50.2 g (yield: 96.5%) of compound (3-1).

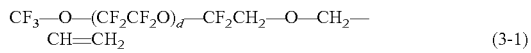

$$CF_3—O—(CF_2CF_2O)_d—CF_2CH_2—O—CH_2—CH=CH_2 \quad (3\text{-}1)$$

NMR spectrum of compound (3-1);
$^1$H-NMR (300.4 MHz, solvent: CDCl$_3$, standard: TMS) δ (ppm): 3.8 (2H), 4.1 (2H), 5.2 to 5.3 (2H), 5.9 (1H).
$^{19}$F-NMR (282.7 MHz, solvent: CDCl$_3$, standard: CFCl$_3$) δ (ppm): −56.3 (3F), −78.3 (2F), −89.5 (26F), −91.5 (2F).
The average value of the number of units d: 7.
The number average molecular weight of compound (3-1): 1,000.

Production Example 2: Production of Compound (3-2)

The following compound (3-2) was obtained by the method in Ex. 7 in WO2013/121986.

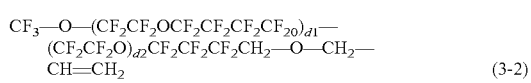

$$CF_3—O—(CF_2CF_2OCF_2CF_2CF_2CF_2O)_{d1}—(CF_2CF_2O)_{d2}CF_2CF_2CF_2CH_2—O—CH_2—CH=CH_2 \quad (3\text{-}2)$$

NMR spectrum of compound (3-2);
$^1$H-NMR (300.4 MHz, solvent: CDCl$_3$, standard: TMS) δ (ppm): 3.8 (2H), 4.1 (2H), 5.2 (2H), 5.9 (1H).
$^{19}$F-NMR (282.7 MHz, solvent: CDCl$_3$, standard: CFCl$_3$) δ (ppm): −56.2 (3F), −84.1 (54F), −89.3 (54F), −91.4 (2F), −120.5 (2F), −126.6 (52F), −128.6 (2F).
The average value of the number of units d1: 13.
The average value of the number of units d2: 1
The number average molecular weight of compound (3-2): 4,700.

Production Example 3: Production of Compound (3-3)

In a two-necked eggplant flask of 100 mL, 30.0 g of the following compound (3-3a) (FLUOROLINK D4000: trade name, manufactured by Solvay Solexis), 0.64 g of tetrabutylammonium hydrogen sulfate, 4.5 g of allyl bromide and 6.0 g of a 30% sodium hydroxide aqueous solution were added and stirred at 60° C. for 8 hours. After completion of the reaction, 30 g of AC-2000 was added, followed by washing once with a dilute aqueous hydrochloric acid solution to recover the organic phase. The recovered organic phase was passed through a silica gel column, and the recovered solution was concentrated by an evaporator to obtain 29.7 g (yield: 97.1%) of compound (3-3).

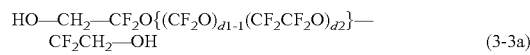

$$HO—CH_2—CF_2O\{(CF_2O)_{d1\text{-}1}(CF_2CF_2O)_{d2}\}—CF_2CH_2—OH \quad (3\text{-}3a)$$

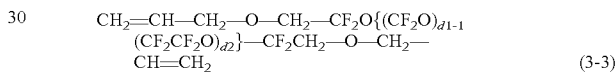

$$CH_2=CH—CH_2—O—CH_2—CF_2O\{(CF_2O)_{d1\text{-}1}(CF_2CF_2O)_{d2}\}—CF_2CH_2—O—CH_2—CH=CH_2 \quad (3\text{-}3)$$

NMR spectrum of compound (3-3);
$^1$H-NMR (300.4 MHz, solvent: CDCl$_3$, standard: TMS) δ (ppm): 3.7 (4H), 4.1 (4H), 5.2 to 5.3 (4H), 5.9 (2H).
$^{19}$F-NMR (282.7 MHz, solvent: CDCl$_3$, standard: CFCl$_3$) δ (ppm): −52.3 to −55.7 (42F), −78.1 (2F), −80.2 (2F), −89.4 to −91.1 (84F).
The average value of the number of units (d1-1): 21.
The average value of the number of units d2: 21.
The number average molecular weight of compound (3-3): 4,100.

Production Example 4: Production of Compound (3-4)

In a three-necked flask of 300 mL, 2.9 g of a 20% KOH aqueous solution, 33 g of tert-butyl alcohol, 110 g of 1,3-bis(trifluoromethyl)benzene and 220 g of compound (3-3a) were put, and 14.6 g of CF$_3$CF$_2$CF$_2$—O—CF=CF$_2$ was added. Under a nitrogen atmosphere, the mixture was stirred at 40° C. for 20 hours. It was washed once with a dilute aqueous hydrochloric acid solution, and the organic phase was recovered and concentrated by an evaporator to obtain 233 g of a crude product (a). The crude product (a) was diluted with 115 g of AC-2000 and developed by silica gel column chromatography for fractionation. As the developing solvents, AC-2000, AC-2000/CF$_3$CH$_2$OCF$_2$CF$_2$H (AE-3000: trade name, manufactured by Asahi Glass Company, Limited) (mass ratio: 1/2), and AE-3000/acetone (mass ratio: 2/1) were sequentially used. With respect to each fraction, the structure of terminal groups and the average values of the numbers of units of constituting units (d1, d2) were obtained from the integral values of $^1$H-NMR and $^{19}$F-NMR. Thus, it was found that in the crude product (a), compound (3-4a), compound (3-4b) and compound (3-3a) were contained in amounts of 50 mol %, 25 mol % and 25 mol %, respectively. Here, 105.1 g (yield: 44.8%) of compound (3-4a) was obtained.

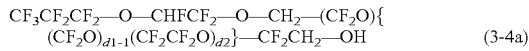
(3-4a)

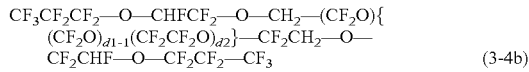
(3-4b)

NMR spectrum of compound (3-4a);
$^1$H-NMR (300.4 MHz, solvent: CDCl$_3$, standard: TMS) δ (ppm): 3.9 (2H), 4.2 (2H), 5.8 to 6.0 (1H).
$^{19}$F-NMR (282.7 MHz, solvent: CDCl$_3$, standard: CFCl$_3$) δ (ppm): −52.4 to −55.8 (42F), −78.8 (1F), −80.8 (1F), −81.4 (1F), −82.2 (3F), −83.5 (1F), −85.3 to −88.2 (2F), −89.4 to −91.1 (86F), −130.5 (2F), −145.1 (1F).
The average value of the number of units (d1-1): 21.
The average value of the number of units d2: 21.
The number average molecular weight of compound (3-4a): 4,300.

NMR spectrum of compound (3-4b);
$^1$H-NMR (300.4 MHz, solvent: CDCl$_3$, standard: TMS) δ (ppm): 4.2 (4H), 5.8 to 6.0 (2H).
$^{19}$F-NMR (282.7 MHz, solvent: CDCl$_3$, standard: CFCl$_3$) δ (ppm): −52.4 to −55.8 (42F), −78.8 (2F), −80.7 (2F), −82.2 (6F), −85.3 to −88.2 (4F), −89.4 to −91.1 (88F), −130.5 (4F), −145.1 (2F).
The average value of the number of units (d1-1): 21.
The average value of the number of units d2: 21.
The number average molecular weight of compound (3-4b): 4,500.

In a two-necked eggplant flask of 100 mL, 52.0 g of compound (3-4a), 0.52 g of tetrabutylammonium hydrogen sulfate, 4.4 g of allyl bromide and 6.5 g of a 30% sodium hydroxide aqueous solution were added and stirred at 60° C. for 8 hours. After completion of the reaction, 50 g of AC-2000 was added, followed by washing once with a dilute aqueous hydrochloric acid solution to recover the organic phase. The recovered organic phase was passed through a silica gel column, and the recovered solution was concentrated by an evaporator to obtain 52.4 g (yield: 99.9%) of compound (3-4).

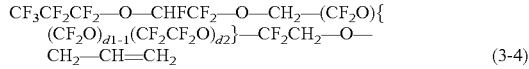
(3-4)

NMR spectrum of compound (3-4);
$^1$H-NMR (300.4 MHz, solvent: CDCl$_3$, standard: TMS) δ (ppm): 3.7 (2H), 4.1 (2H), 4.2 (2H), 5.2 to 5.3 (2H), 5.8 to 6.0 (2H).
$^{19}$F-NMR (282.7 MHz, solvent: CDCl$_3$, standard: CFCl$_3$) δ (ppm): −52.3 to −55.7 (42F), −78.1 (1F), −78.7 (1F), −80.2 (1F), −80.7 (1F), −82.2 (3F), −85.4 to −88.2 (2F), −89.4 to −91.1 (86F), −130.5 (2F), −145.1 (1F).
The average value of the number of units (d1-1): 21.
The average value of the number of units d2: 21.
The number average molecular weight of compound (3-4): 4,300.

Production Example 5: Synthesis of Mixture (3-5)

In a two-necked eggplant flask of 100 mL, 26.0 g of the crude product (a) obtained in Production Example 4, 0.26 g of tetrabutylammonium hydrogen sulfate, 2.2 g of allyl bromide and 3.3 g of a 30% sodium hydroxide aqueous solution were added and stirred at 60° C. for 8 hours. After completion of the reaction, 30 g of AC-2000 was added, followed by washing once with a dilute aqueous hydrochloric acid solution to recover the organic phase. The recovered organic phase was passed through a silica gel column, and the recovered solution was concentrated by an evaporator to obtain 26.1 g (yield: 99.0%) of mixture (3-5).

Mixture (3-5) is a mixture of compound (3-3), compound (3-4) and compound (3-4b) in a ratio of 25:50:25 (mol %).

Production Example 6: Synthesis of Compound (3-6)

In an eggplant flask of 100 mL, 30.0 g of compound (3-4a), 0.9 g of sodium fluoride powder and 30 g of dichloropentafluoropropane (AK-225: trade name, manufactured by Asahi Glass Company, Limited) were put, and 3.5 g of CF$_3$CF$_2$CF$_2$OCF(CF$_3$)COF was added. Under a nitrogen atmosphere, the mixture was stirred at 50° C. for 24 hours. After removing the sodium fluoride powder by a pressure filter, excess CF$_3$CF$_2$CF$_2$OCF(CF$_3$)COF and AK-225 were distilled off under reduced pressure. The obtained crude product was diluted with AC-2000 and passed through a silica gel column, and the recovered solution was concentrated by an evaporator to obtain 31.8 g (yield: 98.8%) of compound (3-6d).

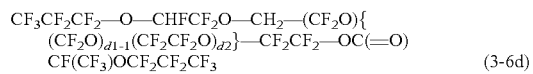
(3-6d)

NMR spectrum of compound (3-6d);
$^1$H-NMR (300.4 MHz, solvent: CDCl$_3$, standard: TMS) δ (ppm): 4.2 (2H), 4.7 (2H), 5.8 to 6.0 (1H).
$^{19}$F-NMR (282.7 MHz, solvent: CDCl$_3$, standard: CFCl$_3$) δ (ppm): −52.4 to −55.8 (42F), −78.8 to −88.2 (17F), −89.4 to −91.1 (86F), −130.3 (2F), −30.5 (2F), −132.5 (1F), −145.1 (1F).
The average value of the number of units (d1-1): 21.
The average value of the number of units d2: 21.
The number average molecular weight of compound (3-6d): 4,500.

An autoclave (made of nickel, inner volume: 1 L) was prepared, and at a gas outlet of the autoclave, a condenser kept at 20° C., a NaF pellet packed layer and a condenser kept at 0° C. were set in series. Further, a liquid returning line for returning a condensed liquid from the condenser kept at 0° C. to the autoclave, was installed.

Into the autoclave, 750 g of ClCF$_2$CFClCF$_2$OCF$_2$CF$_2$Cl (hereinafter referred to also as "CFE-419") was charged and stirred while maintaining the temperature at 25° C. Into the autoclave, nitrogen gas was blown at 25° C. for 1 hour, and then, 20% fluorine gas was blown at 25° C. for one hour at a flow rate of 2.0 L/hr. Then, while blowing 20% fluorine gas at the same flow rate, into the autoclave, a solution having 31.0 g of compound (3-6d) dissolved in 124 g of CFE-419, was injected over a period of 4.3 hours.

Then, while blowing 20% fluorine gas at the same flow rate, the internal pressure of the autoclave was pressurized up to 0.15 MPa (gauge pressure). Into the autoclave, 4 mL of a benzene solution containing 0.05 g/mL of benzene in CFE-419, was injected while heating from 25° C. to 40° C., and the benzene solution inlet of the autoclave was closed. After stirring for 15 minutes, 4 mL of the benzene solution was injected again while maintaining the temperature at 40° C., and the inlet was closed. The same operation was repeated three more times. The total amount of benzene injected was 0.17 g.

Further, while blowing 20% fluorine gas at the same flow rate, stirring was continued for 1 hour. Then, the pressure in the autoclave was returned to the atmospheric pressure, and nitrogen gas was blown for 1 hour. The content of the autoclave was concentrated by an evaporator to obtain 31.1 g (yield: 98.5%) of compound (3-6c).

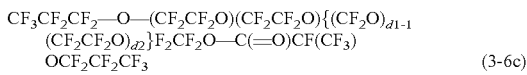
(3-6c)

NMR spectrum of compound (3-6c);
$^{19}$F-NMR (282.7 MHz, solvent: CDCl$_3$, standard: CFCl$_3$) δ (ppm): −52.4 to −55.7 (42F), −78.8 to −88.1 (11F), −89.4 to −91.1 (96F), −91.5 (2F), −130.3 (2F), −130.5 (2F), −132.5 (1F).

The average value of the number of units (d1-1): 21.
The average value of the number of units d2: 21.
The number average molecular weight of compound (3-6c): 4,600.

Into a round bottomed flask made of PFA, 30.0 g of compound (3-6c) and 60 g of AK-225 were charged. While stirring under cooling in an ice bath, under a nitrogen atmosphere, 2.0 g of methanol was slowly added dropwise from a dropping funnel. While bubbling with nitrogen, stirring was continued for 12 hours. The reaction mixture was concentrated by an evaporator to obtain 27.6 g (yield: 98.8%) of compound (3-6b).

(3-6b).

NMR spectrum of compound (3-6b);
$^{1}$H-NMR (300.4 MHz, solvent: CDCl$_3$, standard: TMS) δ (ppm): 3.9 (3H).
$^{19}$F-NMR (282.7 MHz, solvent: CDCl$_3$, standard: CFCl$_3$) δ (ppm): −52.4 to −55.8 (42F), −82.2 (3F), −89.4 to −91.1 (92F), −130.5 (2F).

The average value of the number of units (d1-1): 21.
The average value of the number of units d2: 21.
The number average molecular weight of compound (3-6b): 4,300.

In a three-necked round-bottomed flask of 100 mL, 0.18 g of lithium chloride was dissolved in 18.3 g of ethanol. To this, 25.0 g of compound (3-6b) was added, and while cooling in ice bath, a solution having 0.75 g of sodium borohydride dissolved in 22.5 g of ethanol was slowly dropwise added. Then, the ice bath was removed, and stirring was continued while slowly warming to room temperature. After stirring at room temperature for 12 hours, an aqueous solution of hydrochloric acid was dropwise added until the liquid became acidic. 20 mL of AC-2000 was added, followed by washing once with water and once with a saturated sodium chloride aqueous solution, to recover the organic phase. The recovered organic phase was concentrated by an evaporator to obtain 24.6 g (yield: 99.0%) of compound (3-6a).

(3-6a).

NMR spectrum of compound (3-6a);
$^{1}$H-NMR (300.4 MHz, solvent: CDCl$_3$, standard: TMS) δ (ppm): 3.9 (2H).
$^{19}$F-NMR (282.7 MHz, solvent: CDCl$_3$, standard: CFCl$_3$) δ (ppm): −52.4 to −55.7 (42F), −81.4 (1F), −82.2 (3F), −83.4 (1F), −89.4 to −91.1 (90F), −130.5 (2F).

The average value of the number of units (d1-1): 21.
The average value of the number of units d2: 21.
The number average molecular weight of compound (3-6a): 4,200.

In a two-necked eggplant flask of 100 mL, 20.0 g of compound (3-6a), 0.21 g of tetrabutylammonium hydrogen sulfate, 1.76 g of allyl bromide and 2.6 g of a 30% sodium hydroxide aqueous solution were added and stirred at 60° C. for 8 hours. After completion of the reaction, 20 g of AC-2000 was added, followed by washing once with a dilute aqueous hydrochloric acid solution to recover the organic phase. The recovered organic phase was passed through a silica gel column, and the recovered solution was concentrated by an evaporator to obtain 19.8 g (yield: 98.2%) of compound (3-6).

(3-6).

NMR spectrum of compound (3-6);
$^{1}$H-NMR (300.4 MHz, solvent: CDCl$_3$, standard: TMS) δ (ppm): 3.7 (2H), 4.1 (2H), 5.2 to 5.3 (2H), 5.9 (1H).
$^{19}$F-NMR (282.7 MHz, solvent: CDCl$_3$, standard: CFCl$_3$) δ (ppm): −52.3 to −55.7 (42F), −78.1 (1F), −80.1 (1F), −82.1 (3F), −89.4 to −91.1 (94F), −130.5 (2F).

The average value of the number of units (d1-1): 21.
The average value of the number of units d2: 21.
The number average molecular weight of compound (3-6): 4,300.

[Compound (4)]
As compound (4), the following compounds were used.
Compound (4-1): HSi(OCH$_3$)$_3$.
Compound (4-2): HSi(CH$_3$)(OCH$_3$)$_2$.

[Transition Metal Catalyst (C)]
As transition metal catalyst (C), the following compounds were used.
Transition metal catalyst (C1): Pt/divinyltetramethyldisiloxane complex (2.0% xylene solution).
Transition metal catalyst (C2): Pt/tetramethyltetravinylcyclotetrasiloxane complex (1.8% vinyl methyl cyclotetrasiloxane solution).

[Compound (D)]
As compound (D), the following compounds were used.
DMSO: dimethyl sulfoxide.
TMSO: tetramethylene sulfoxide.
HMPA: hexamethylphosphoramide.
DMF: N,N-dimethylformamide.
Aniline.
Pyridine.
Tetra methyl urea.

[Fluorinated Organic Solvent (E)]
As fluorinated organic solvent (E), the following compounds were used.
Fluorinated organic solvent (E1): AC-2000.
Fluorinated organic solvent (E2): AC-6000.

Ex. 1 to 13, 21 to 26: Production of Fluorinated Ether Compositions

Into a sample bottle made of PP or a flask made of PFA, compound (3), compound (4), transition metal catalyst (C), compound (D) and fluorinated organic solvent (E) in the charged amounts as shown in Table 1 and Table 2 and a stirrer, were put, sealed and reacted at reaction conditions as shown in Table 1 and Table 2, to obtain the respective compositions (1) to (13) and (21) to (26). In this specification, the term "room temperature" is from 20 to 30° C. Further, the composition obtained in Ex. 1 is identified as "composition (1)", and compositions obtained in other Ex. are likewise identified.

The number average molecular weight (Mn) of each of the obtained compositions (1) to (13) and (21) to (26) was measured by the method as described above. Further, the conversion and selectivity of the reaction for each of the obtained compositions (1) to (13) and (21) to (26) were calculated by $^1$H-NMR analysis. Further, the proportion of each of groups (2-1) to (2-4) to the total number of moles of groups (2-1) to (2-4) in each composition, was also obtained. The results are shown in Table 3 and Table 4.

Here, transition metal catalyst (C1) and transition metal catalyst (C2) were added in the form of a solution, as mentioned above. In the description of transition metal catalyst (C) in Table 1 and Table 2, "mg (solution)" means the mass as the solution, and "μg (catalyst)" means the net amount of transition metal catalyst.

Further, the conversion and selectivity mean the following.

Conversion: When compound (2-1) having group (2-1) and compound (2-4) having group (2-4) (comprising a cis-form and a trans form) are produced from compound (2-3) having group (2-3), a value obtained by dividing the number of moles of the total of group (2-1) and group (2-4) by the number of moles further including group (2-3), is represented as a numerical value by percentage.

Selectivity: A value obtained by dividing the number of moles of group (2-1) by the total number of moles of group (2-1) and (2-4), is represented by a numerical value by percentage.

TABLE 1

| | Compound (3) | | | Compound (4) | | | Transition metal catalyst (C) | | Compound (D) | | Fluorinated organic solvent (E) | | Reaction conditions | | (Mn) of obtained com- |
| | | | | | | | mg (solu-tion) | μm (cata-lyst) | | | | | | | |
| Ex. | Type | g | mmol | Type | g | mmol | Type | | | Type | mg | Type | g | Temp. | Time | position |
| 1 | 3-1 | 1.00 | 0.98 | 4-1 | 0.30 | 2.46 | C1 | 1.0 | 20 | DMSO | 1.0 | E1 | 0.50 | Room temp. | 4 | 1,100 |
| 2 | 3-1 | 1.00 | 0.98 | 4-1 | 0.30 | 2.46 | C1 | 1.0 | 20 | TMSO | 1.0 | E1 | 0.50 | Room temp. | 4 | 1,100 |
| 3 | 3-1 | 1.00 | 0.98 | 4-1 | 0.30 | 2.46 | C1 | 1.0 | 20 | Aniline | 1.0 | E1 | 0.50 | Room temp. | 4 | 1,100 |
| 4 | 3-1 | 1.00 | 0.98 | 4-1 | 0.30 | 2.46 | C1 | 1.0 | 20 | Pyridine | 1.0 | E1 | 0.50 | Room temp. | 12 | 1,100 |
| 5 | 3-1 | 1.00 | 0.98 | 4-1 | 0.30 | 2.46 | C1 | 1.0 | 20 | Tetra-methyl urea | 1.0 | E1 | 0.50 | Room temp. | 12 | 1,100 |
| 6 | 3-1 | 1.00 | 0.98 | 4-1 | 0.30 | 2.46 | C1 | 1.0 | 20 | HMPA | 1.0 | E1 | 0.50 | Room temp. | 24 | 1,100 |
| 7 | 3-1 | 1.00 | 0.98 | 4-2 | 0.15 | 1.42 | C1 | 0.5 | 10 | DMSO | 0.2 | E2 | 0.10 | Room temp. | 8 | 1,100 |
| 8 | 3-1 | 1.00 | 0.98 | 4-1 | 0.30 | 2.46 | C2 | 1.1 | 20 | DMSO | 1.0 | — | — | Room temp. | 4 | 1,100 |
| 9 | 3-2 | 1.00 | 0.21 | 4-1 | 0.06 | 0.49 | C1 | 1.0 | 20 | DMSO | 1.0 | E1 | 0.50 | Room temp. | 4 | 4,800 |
| 10 | 3-3 | 1.00 | 0.24 | 4-1 | 0.10 | 0.82 | C1 | 1.0 | 20 | DMSO | 1.0 | E1 | 0.50 | Room temp. | 4 | 4,200 |
| 11 | 3-4 | 1.00 | 0.23 | 4-1 | 0.05 | 0.41 | C1 | 1.0 | 20 | DMSO | 1.0 | E1 | 0.50 | Room temp. | 4 | 4,400 |
| 12 | 3-5 | 1.00 | 0.23 | 4-1 | 0.05 | 0.41 | C1 | 1.0 | 20 | DMSO | 1.0 | E1 | 0.50 | Room temp. | 4 | 4,400 |
| 13 | 3-6 | 1.00 | 0.23 | 4-1 | 0.05 | 0.41 | C1 | 1.0 | 20 | DMSO | 1.0 | E1 | 0.50 | Room temp. | 4 | 4,400 |

TABLE 2

| | Compound (3) | | | Compound (4) | | | Transition metal catalyst (C) | | Compound (D) | | Fluorinated organic solvent (E) | | Reaction conditions | | (Mn) of obtained com- |
| | | | | | | | mg (solu-tion) | μm (cata-lyst) | | | | | | | |
| Ex. | Type | g | mmol | Type | g | mmol | Type | | | Type | mg | Type | g | Temp. | Time | position |
| 21 | 3-4 | 5.00 | 1.16 | 4-1 | 0.20 | 1.64 | C1 | 5.0 | 100 | — | — | E1 | 2.50 | 80 | 8 | 4,400 |
| 22 | 3-4 | 10.0 | 2.33 | 4-1 | 0.31 | 2.54 | C1 | 10.0 | 200 | DMF | 10.0 | E1 | 1.16 | 40 | 4 | 4,400 |
| 23 | 3-4 | 5.00 | 1.16 | 4-1 | 0.140 | 1.15 | C1 | 1.0 | 20 | DMSO | 10.0 | — | — | 40 | 4 | 4,400 |
| 24 | 3-4 | 5.00 | 1.16 | 4-1 | 0.130 | 1.07 | C1 | 1.0 | 20 | DMSO | 10.0 | — | — | 40 | 4 | 4,400 |
| 25 | 3-4 | 5.00 | 1.16 | 4-1 | 0.120 | 0.98 | C1 | 1.0 | 20 | DMSO | 10.0 | — | — | 40 | 4 | 4,400 |
| 26 | 3-4 | 10.0 | 2.33 | 4-1 | 0.31 | 2.54 | C1 | 2.0 | 40 | DMSO | 2.0 | E2 | 0.40 | 40 | 4 | 4,400 |

TABLE 3

| | Reaction performance | | Proportion of each group to the total number of moles of groups (2-1) to (2-4) | | | |
|---|---|---|---|---|---|---|
| | | | Group | Group | Group | Group |
| Ex. | Conversion (%) | Selectivity (%) | (2-1) | (2-2) | (2-3) | (2-4) |
| | | | (mol %) | | | |
| 1 | 100 | 96 | 96 | 0 | 0 | 4 |
| 2 | 96 | 96 | 92 | 0 | 4 | 4 |
| 3 | 100 | 96 | 96 | 0 | 0 | 4 |
| 4 | 100 | 92 | 92 | 0 | 0 | 8 |
| 5 | 100 | 90 | 90 | 0 | 0 | 10 |
| 6 | 100 | 90 | 90 | 0 | 0 | 10 |
| 7 | 100 | 96 | 96 | 0 | 0 | 4 |
| 8 | 100 | 96 | 96 | 0 | 0 | 4 |
| 9 | 98 | 97 | 95 | 0 | 2 | 3 |
| 10 | 100 | 96 | 96 | 0 | 0 | 4 |
| 11 | 100 | 95 | 95 | 0 | 0 | 5 |
| 12 | 100 | 96 | 96 | 0 | 0 | 4 |
| 13 | 99 | 96 | 95 | 0 | 1 | 4 |

TABLE 4

| | Reaction performance | | Proportion of each group to the total number of moles of groups (2-1) to (2-4) | | | |
|---|---|---|---|---|---|---|
| | | | Group | Group | Group | Group |
| Ex. | Conversion (%) | Selectivity (%) | (2-1) | (2-2) | (2-3) | (2-4) |
| | | | (mol %) | | | |
| 21 | 100 | 81 | 81 | 0 | 0 | 19 |
| 22 | 100 | 86 | 86 | 0 | 0 | 14 |
| 23 | 95 | 97 | 92 | 0 | 5 | 3 |
| 24 | 90 | 96 | 86 | 0 | 10 | 4 |
| 25 | 83 | 96 | 80 | 0 | 17 | 3 |
| 26 | 100 | 95 | 95 | 0 | 0 | 5 |

In Ex. 1 to 13, 23 and 26, the conversion and selectivity were high, and it was possible to obtain compositions wherein the proportion of group (2-1) was from 90 to 99 mol %, the proportion of group (2-2) was from 0 to 9 mol %, the proportion of group (2-3) was from 0 to 9 mol %, and the proportion of group (2-4) was from 1 to 10 mol %.

The selectivity was highest in Ex. using, as compound (D), DMSO and TMSO being a sulfoxide compound, and aniline being an aromatic amine compound, and then, was high in Ex. using, as compound (D), aniline and pyridine being an aromatic amine compound and tetramethyl urea and HMPA being a nitrogen-containing compound.

Ex. 27: Production of Fluorinated Ether Composition

Into a 50 mL sealed-type pressure vessel made of polytetrafluoroethylene, 5.0 g of compound (3-4), 0.034 g of di-tert-butyl peroxide, 1.26 g of trichlorosilane and 2.5 g of AC-2000 were put and stirred at 120° C. for 8 hours. After distilling off unreacted reactants, solvent, etc. by concentration under reduced pressure, the reaction solution was placed in a flask equipped with a dropping funnel, and 1.0 g of a mixed solution of trimethyl orthoformate and methanol (trimethyl orthoformate/methanol=25/1 molar ratio) was added dropwise, and allowed to react at 60° C. for 3 hours.

By the $^1$H-NMR analysis of the obtained composition, the proportion of each of groups (2-1) to (2-4) to the total number of moles of groups (2-1) to (2-4) in the composition, was obtained. The results are shown in Table 5. Further, the number average molecular weight (Mn) of the obtained composition was 4,400.

In Ex. 27, as shown in Table 5, from compound (2-3), compound (2-1) and compound (2-2) were formed. Therefore, the conversion in Ex. 27 is a numerical value represented by percentage, of a value obtained by dividing the total number of moles of group (2-1) and group (2-2) by the number of moles further including group (2-3). The selectivity is a numerical value represented by percentage, of a value obtained by dividing the number of moles of group (2-1) by the total number of moles of group (2-1) and group (2-2).

Ex. 31 to 37

By distilling off low-boiling components from the compositions obtained in Ex. 21-27, compositions (31) to (37) were obtained. Here, the amounts (yields) of compositions (21) to (27) in the above reaction were as follows.

Ex. 21: 4.9 g (yield: 95%), Ex. 22: 9.9 g (yield: 96%), Ex. 23: 5.1 g (yield: 99%), Ex. 24: 5.0 g (yield: 97%), Ex. 25: 5.0 g (yield: 97%), Ex. 26: 10.1 g (yield: 98%), Ex. 27: 5.0 g (yield: 97%).

Each yield of the above is a weight yield when the product is assumed to be a compound having group (2-1).

Further, the appearance of compositions (31) to (37) was as follows.

Ex. 31: yellow transparent liquid, Ex. 32: pale yellow transparent liquid, Ex. 33 to 37: colorless transparent liquid.

In Ex. 31 and Ex. 32, the amount of catalyst was large, whereby coloration which is considered to be attributable to the catalyst, was observed. In Ex. 33 to 36, the amount of catalyst was relatively small, and it is considered that the reaction proceeded under mild reaction conditions whereby there was no coloration.

Using each of compositions (31) to (37) after distilling off low boiling point components, surface treatment of a substrate was conducted to form a surface-treated layer on the substrate. As the surface treatment method, the following dry coating and wet coating methods were, respectively, used for each Ex. As the substrate, chemically strengthened glass was used. The substrate having the obtained surface-treated layer was evaluated by the following methods. The results are shown in Table 5.

Dry Coating Method

The dry coating was conducted by means of a vacuum vapor deposition apparatus (VTR-350M, manufactured by ULVAC, Inc.) (vacuum vapor deposition method). 0.5 g of a composition obtained in each Ex. was charged into a molybdenum boat in the vacuum vapor deposition apparatus, and the inside of the vacuum vapor deposition apparatus was evacuated to at most $1 \times 10^{-3}$ Pa. The boat having the composition placed thereon was heated at a temperature raising rate of at most 10° C./min, and when the deposition rate by a quartz oscillator film thickness meter exceeded 1 nm/sec., the shutter was opened to initiate film deposition on the surface of a substrate. When the film thickness became about 50 nm, the shutter was closed to terminate film deposition on the surface of the substrate. The substrate having the composition deposited thereon, was heat treated at 200° C. for 30 minutes, followed by washing with AK-225, to obtain the substrate having a surface-treated layer.

Wet Coating Method

A composition in each Ex. and $C_4F_9OC_2H_5$ (Novec-7200: trade name, manufactured by 3M Company) as a liquid medium were mixed to prepare a coating liquid having a solid content concentration of 0.05%. A substrate was dipped in the coating liquid (dip coating method) and left to stand for 30 minutes, whereupon the substrate was pulled out. The substrate was dried at 200° C. for 30 minutes, followed by washing with AK-225, to obtain the substrate having a surface-treated layer.

Evaluation Method in Dry Coating Method and Wet Coating Method

<Method for Measuring Water Contact Angle and n-hexadecane Contact Angle>

A contact angle of about 2 μL of distilled water or n-hexadecane placed on the surface of the surface-treated layer, was measured by means of a contact angle measuring apparatus DM-500 (manufactured by Kyowa Interface Science Co., Ltd.). Measurements are performed at five different locations on the surface of the surface-treated layer of the substrate, and the average value was calculated. For the calculation of the contact angle, a 2θ method was used.

<Initial Water and n-hexadecane Contact Angles>

With respect to a substrate having a surface-treated layer, the initial water contact angle and n-hexadecane contact angles were measured by the above measuring method.

<Abrasion Resistance 1>

With respect to a substrate having a surface-treated layer, using a reciprocating traverse testing machine (manufactured by KNT Co., Ltd.) in accordance with JIS L0849, a cellulose non-woven fabric (BEMCOT M-3, manufactured by Asahi Kasei Corporation) was reciprocated 100,000 times and 200,000 times under a load of 1 kg, whereupon the water contact angle and n-hexadecane contact angle were measured.

The smaller the decrease in water repellency (water contact angle) and oil repellency (n-hexadecane contact angle) when the number of abrasion times is increased, the smaller the decrease in performance due to the abrasion, and the better the abrasion resistance.

<Abrasion Resistance 2>

With respect to a substrate having a surface-treated layer obtained by the wet coating method, using a steel wool Bon Star (#0000), it was reciprocated under a load of 1 kg/cm$^2$ at a speed 320 cm/min, 2,000 times and 5,000 times, whereupon the water contact angle was measured.

The smaller the decrease in water repellency (water contact angle) when the number of abrasion times is increased, the smaller the decrease in performance due to abrasion, and the better the abrasion resistance.

<Fingerprint Stain Removability>

An artificial fingerprint liquid (liquid consisting of oleic acid and squalene) was deposited on a flat surface of a silicon rubber plug, and then, excess oil was wiped off by a nonwoven fabric (BEMCOT M-3, manufactured by Asahi Kasei Corporation), to prepare a fingerprint stamp. The fingerprint stamp was placed on a substrate having a surface-treated layer and pressed under a load of 1 kg for 10 seconds. At that time, the haze at a portion where the fingerprint was adhered, was measured by a haze meter (manufactured by Toyo Seiki Seisaku-Sho, Ltd.). The value at that time was taken as the initial value. Then, the portion where the fingerprint was adhered, was subjected to wiping under a load of 500 g by means of a reciprocating traverse testing machine (manufactured by KNT Co., Ltd.) having tissue paper attached. The value of the haze was measured every one wiping reciprocation, and a case where a numerical value where the haze is no longer visually observed, was reached within such wiping reciprocations of 10 times, was regarded as "pass".

<Dynamic Friction Coefficient>

The coefficient of dynamic friction against the artificial skin (PBZ13001, manufactured by Idemitsu Techno Fine Co., Ltd.), of a substrate having a surface-treated layer, was measured by means of a load variation type friction wear test system HHS2000 (manufactured by Shinto Scientific Co., Ltd.) under conditions of a contact area of 3 cm×3 cm and a load of 100 g.

The smaller the dynamic friction coefficient, the better the lubricity.

TABLE 5

| | | | Ex. | | | | | | |
|---|---|---|---|---|---|---|---|---|---|
| | | | 31 | 32 | 33 | 34 | 35 | 36 | 37 |
| | | | Composition to be used | | | | | | |
| | | | 21 | 22 | 23 | 24 | 25 | 26 | 27 |
| | | | Molar ratio Group (2-1)/group (2-2)/group (2-3)/group (2-4) | | | | | | |
| | | | 81/0/0/19 | 86/0/0/14 | 92/0/5/3 | 86/0/10/4 | 80/0/17/3 | 95/0/0/5 | 92/8/0/0 |
| Dry coating method | Water contact angle (degrees) | Initial | 112.0 | 112.3 | 111.8 | 112.0 | 111.6 | 112.2 | 110.9 |
| | | Abrasion resistance 1 (after 100,000 times) | 111.4 | 112.0 | 111.4 | 111.1 | 111.3 | 111.9 | 110.3 |
| | | Abrasion resistance 1 (after 200,000 times) | 92.7 | 108.2 | 111.2 | 106.5 | 97.6 | 111.1 | 90.5 |
| | n-Hexadecane contact angle (degrees) | Initial | 64.8 | 65.2 | 65.5 | 65.3 | 65.3 | 65.0 | 65.2 |
| | | Abrasion resistance 1 (after 100,000 times) | 64.5 | 64.4 | 64.3 | 64.0 | 64.9 | 64.5 | 64.8 |
| | | Abrasion resistance 1 (after 200,000 times) | 60.2 | 64.2 | 63.5 | 62.8 | 62.6 | 64.6 | 55.5 |
| | Fingerprint stain removability | | Pass | Pass | Pass | Pass | Pass | Pass | Pass |
| | Dynamic friction coefficient | | 0.24 | 0.24 | 0.25 | 0.23 | 0.23 | 0.25 | 0.26 |
| Wet coating method | Water contact angle (degrees) | Initial | 110.8 | 111.7 | 111.9 | 111.2 | 112.2 | 112.0 | 110.1 |
| | | Abrasion resistance 1 (after 100,000 times) | 110.8 | 111.4 | 110.0 | 110.9 | 110.4 | 111.5 | 109.8 |
| | | Abrasion resistance 1 (after 200,000 times) | 88.6 | 103.5 | 107.1 | 106.0 | 93.4 | 110.8 | 85.6 |
| | | Abrasion resistance 2 (after 2,000 times) | 97.1 | 97.6 | 107.3 | 103.7 | 105.9 | 106.3 | 106.9 |

TABLE 5-continued

| | | Ex. 31 | Ex. 32 | Ex. 33 | Ex. 34 | Ex. 35 | Ex. 36 | Ex. 37 |
|---|---|---|---|---|---|---|---|---|
| | | \multicolumn{7}{c}{Composition to be used} |
| | | 21 | 22 | 23 | 24 | 25 | 26 | 27 |
| | | \multicolumn{7}{c}{Molar ratio Group (2-1)/group (2-2)/group (2-3)/group (2-4)} |
| | | 81/0/0/19 | 86/0/0/14 | 92/0/5/3 | 86/0/10/4 | 80/0/17/3 | 95/0/0/5 | 92/8/0/0 |
| | Abrasion resistance 2 (after 5,000 times) | 45.0 | 51.8 | 105.4 | 94.2 | 68.1 | 104.0 | 105.3 |
| n-Hexadecane contact angle (degrees) | Initial | 65.3 | 65.5 | 65.5 | 65.9 | 65.6 | 66.0 | 65.4 |
| | Abrasion resistance 1 (after 100,000 times) | 65.0 | 65.4 | 64.9 | 65.5 | 65.0 | 65.2 | 64.8 |
| | Abrasion resistance 1 (after 200,000 times) | 55.0 | 64.9 | 64.5 | 64.4 | 59.9 | 64.0 | 50.1 |
| | Fingerprint stain removability | Pass | Pass | Pass | Pass | Pass | Pass | Pass |
| | Dynamic friction coefficient | 0.30 | 0.30 | 0.30 | 0.29 | 0.30 | 0.31 | 0.32 |

In Ex. 33 and 36, the initial water/oil repellency was high, and the surface-treated layer was excellent in abrasion resistance, fingerprint stain removability and lubricity. Also in abrasion resistance 2 which was carried out under severe friction conditions, no large reduction in water repellency (water contact angle) was observed.

On the other hand, in Ex. 31, 32, 34 and 35 using a composition wherein group (2-1) was less than 90 mol %, the abrasion resistance of the surface-treated layer was poor, and particularly in abrasion resistance 2, the reduction of water repellency (water contact angle) due to an increase in the number of abrasion times was remarkable.

Further, in Ex. 37 wherein although the content of group (2-1) was at least 90 mol %, no group (2-4) was contained, and group (2-2) was contained, the initial abrasion resistance of the surface-treated layer was low, and at the same time, the performance degradation in abrasion resistance 1 was substantial.

INDUSTRIAL APPLICABILITY

The fluorinated ether composition of the present invention is useful for surface treatment to impart water/oil repellency to a surface of a substrate, such as a member constituting a surface of e.g. a touch panel, to be touched by a finger.

This application is a continuation of PCT Application No. PCT/JP2014/082648, filed on Dec. 10, 2014, which is based upon and claims the benefit of priority from Japanese Patent Application No. 2013-258414 and Japanese Patent Application No. 2013-258415 filed on Dec. 13, 2013. The contents of those applications are incorporated herein by reference in their entireties.

What is claimed is:

1. A fluorinated ether composition, comprising:
at least three fluorinated ether compounds of the formula (1) having different group $B^{10}$,
wherein, of the total of group $B^{10}$ present in the composition, a proportion of a group of the formula (2-1) is from 90 to 99 mol %, a proportion of a group of the formula (2-2) is from 0 to 9 mol %, a proportion of a group of the formula (2-3) is from 0 to 9 mol %, and a proportion of a group of the formula (2-4) is from 1 to 10 mol %:

$$A\text{-}O\text{-}Q\text{-}(C_bF_{2b}O)_d\text{---}X\text{---}O\text{---}B^{10} \quad (1)$$

wherein in the formula (1),
A: a $C_{1-20}$ perfluoroalkyl group or $B^{10}$,
Q: a single bond, —$CH_2$—, —CHF—, -$Q^1$-$CH_2$—, -$Q^1$-CHF—, -$Q^1$-O—$CH_2$—, -$Q^1$-O—CHF—, -$Q^1$-$CH_2$—O— or -$Q^1$-CHF—O—,
$Q^1$: a $C_{1-10}$ fluoroalkylene group, a $C_{2-10}$ fluoroalkylene group having an etheric oxygen atom between carbon-carbon atoms, a $C_{10}$ alkylene group, or a $C_{2-10}$ alkylene group having an etheric oxygen atom between carbon-carbon atoms,
b, d: b is an integer of from 1 to 10, and d is an integer of from 1 to 200, provided that when d is at least 2, $(C_bF_{2b}O)_d$ is optionally composed of at least two types of $C_bF_{2b}O$ different in b,
X: a divalent organic group having no $CF_2O$,
$B^{10}$: a group of the formula (2-1), formula (2-2), formula (2-3) or formula (2-4):

$$\text{---}CH_2CH_2CH_2SiL_mR_n \quad (2\text{-}1),$$

$$\text{---}CH_2CH(SiL_mR_n)CH_3 \quad (2\text{-}2),$$

$$\text{---}CH_2CH\text{=}CH_2 \quad (2\text{-}3),$$

$$\text{---}CH\text{=}CHCH_3 \quad (2\text{-}4),$$

wherein in the formulae (2-1) to (2-4),
L: a hydrolysable group,
R: a monovalent hydrocarbon group,
m and n: m is an integer of from 1 to 3, n is an integer of from 0 to 2, and m+n=3.

2. The fluorinated ether composition according to claim 1, wherein of the total of group $B^{10}$ present in the composition, the total proportion of the group of the formula (2-1) and the group of the formula (2-4) is from 95 to less than 100 mol %.

3. The fluorinated ether composition according to claim 2, wherein of the total of group $B^{10}$ present in the composition, the proportion of the group of the formula (2-1) is from 92 to less than 99 mol %, the proportion of the group of the formula (2-2) is from 0 to 5 mol %, the proportion of the group of the formula (2-3) is from 0 to 5 mol %, and the proportion of the group of the formula (2-4) is from 1 to less than 8 mol %.

4. The fluorinated ether composition according to claim 1, wherein A is a $C_{1-20}$ perfluoroalkyl group.

5. A method for producing the fluorinated ether composition of claim 1, comprising:
reacting a compound of the formula (3) and the compound of the formula (4) in the presence of a transition metal catalyst (C) and at least one compound (D) selected from the group consisting of nitrogen-containing compounds and sulfur-containing compounds:

$$A^1\text{-O-Q-}(C_bF_{2b}O)_d\text{—X—O—}B^{20} \quad (3)$$

$$HSiL^1{}_mR_n \quad (4)$$

wherein in the formulae (3) and (4),
$A^1$: the same $C_{1-20}$ perfluoroalkyl group as A in the formula (1) or $B^{20}$,
Q: the same group as Q in the formula (1),
b, d: the same numerical values as b and d in the formula (1), respectively,
X: the same group as X in the formula (1),
$B^{20}$: a group represented by the formula (2-3),
$L^1$: a hydrolyzable group,
R: the same group as R in the formula (1),
m and n: the same numerical values as m and n in the formula (1).

6. The method according to claim 5, wherein the compound (D) is an aromatic amine compound or a sulfoxide compound.

7. The method according to claim 6, wherein the compound (D) is dimethyl sulfoxide or tetramethylene sulfoxide.

8. The method according to claim 5, wherein the transition metal catalyst (C) is a platinum catalyst.

9. The method according to claim 8, wherein the transition metal catalyst (C) is a Pt/divinyltetramethyldisiloxane complex or a Pt/tetramethyltetravinylcyclotetrasiloxane complex.

10. A coating liquid, comprising:
the fluorinated ether composition of claim 1; and
at least one fluorinated organic solvent (E) selected from the group consisting of a fluorinated alkane, a fluorinated aromatic compound and a fluoroalkyl ether.

11. A method for producing a substrate having a surface-treated layer, comprising:
applying the coating liquid of claim 10 to a surface of a substrate, followed by drying.

12. A method for producing a substrate having a surface-treated layer, comprising:
vacuum vapor depositing the fluorinated ether composition of claim 1 on a surface of a substrate.

13. The method according to claim 12, wherein a material of the surface of the substrate is metal, plastic, glass, ceramic or a composite material thereof.

14. A substrate having a surface-treated layer, treated with the fluorinated ether composition of claim 1.

15. A touch panel having, at its input side, a substrate having a surface-treated layer, treated with the fluorinated ether composition of claim 1.

16. The fluorinated ether composition according to claim 1, wherein in the formula (1), Q is —CH$_2$—, —CHF—, -Q$^1$-CH$_2$—, -Q$^1$-CHF—, -Q$^1$-O—CH$_2$—, -Q$^1$-O—CHF—, -Q$^1$-CH$_2$—O— or -Q$^1$-CHF—O—.

17. The fluorinated ether composition according to claim 1, wherein of the total of group $B^{10}$ present in the composition, the proportion of the group of the formula (2-1) is from 92 to less than 99 mol %, the proportion of the group of the formula (2-2) is 0 mol %, the proportion of the group of the formula (2-3) is 5 mol % or less, and the proportion of the group of the formula (2-4) is from 1 to less than 8 mol %.

18. A fluorinated ether composition comprising:
at least two fluorinated ether compounds of the formula (1) having different group $B^{10}$,
wherein, of the total of group $B^{10}$ present in the composition, a proportion of a group of the formula (2-1) is from 90 to 99 mol %, a proportion of a group of the formula (2-2) is from 0 to 9 mol %, a proportion of a group of the formula (2-3) is from 0 to 9 mol %, and a proportion of a group of the formula (2-4) is from 1 to 10 mol %:

$$A\text{-O-Q-}(C_bF_{2b}O)_d\text{—X—O—}B^{10} \quad (1)$$

wherein in the formula (1),
A: a $C_{1-20}$ perfluoroalkyl group or $B^{10}$,
Q is —CH$_2$—, —CH—CH$_2$—CHF—, -Q$^1$-CH$_2$—, -Q$^1$-CHF—, -Q$^1$-O—CH$_2$—, -Q$^1$-O—CHF—, -Q$^1$-CH$_2$—O— or -Q$^1$-CHF—O—,
$Q^1$: a $C_{1-10}$ fluoroalkylene group, a $C_{2-10}$ fluoroalkylene group having an etheric oxygen atom between carbon-carbon atoms, a $C_{1-10}$ alkylene group, or a $C_{2-10}$ alkylene group having an etheric oxygen atom between carbon-carbon atoms,
b, d: b is an integer of from 1 to 10, and d is an integer of from 1 to 200, provided that when d is at least 2, $(C_bF_{2b}O)_d$ is optionally composed of at least two types of $C_bF_{2b}O$ different in b,
X: a divalent organic group having no $CF_2O$,
$B^{10}$: a group of the formula (2-1), formula (2-2), formula (2-3) or formula (2-4):

$$\text{—CH}_2\text{CH}_2\text{CH}_2\text{SiL}_mR_n \quad (2\text{-}1),$$

$$\text{—CH}_2\text{CH(SiL}_mR_n)\text{CH}_3 \quad (2\text{-}2),$$

$$\text{—CH}_2\text{CH=CH}_2 \quad (2\text{-}3),$$

$$\text{—CH=CHCH}_3 \quad (2\text{-}4),$$

wherein in the formulae (2-1) to (2-4),
L: a hydrolysable group,
R: a monovalent hydrocarbon group,
m and n: m is an integer of from 1 to 3, n is an integer of from 0 to 2, and m+n=3.

19. The fluorinated ether composition according to claim 18, wherein of the total of group $B^{10}$ present in the composition, the total proportion of the group of the formula (2-1) and the group of the formula (2-4) is from 95 to 100 mol %.

20. The fluorinated ether composition according to claim 19, wherein of the total of group $B^{10}$ present in the composition, the proportion of the group of the formula (2-1) is from 92 to 99 mol %, the proportion of the group of the formula (2-2) is from 0 to 5 mol %, the proportion of the group of the formula (2-3) is from 0 to 5 mol %, and the proportion of the group of the formula (2-4) is from 1 to 8 mol %.

21. The fluorinated ether composition according to claim 18, wherein A is a $C_{1-20}$ perfluoroalkyl group.

22. A coating liquid, comprising:
the fluorinated ether composition of claim 18; and
at least one fluorinated organic solvent (E) selected from the group consisting of a fluorinated alkane, a fluorinated aromatic compound and a fluoroalkyl ether.

23. A substrate having a surface-treated layer, treated with the fluorinated ether composition of claim 18.

24. A touch panel having, at its input side, a substrate having a surface-treated layer, treated with the fluorinated ether composition of claim 18.

* * * * *